(12) United States Patent
Stone et al.

(10) Patent No.: US 8,337,525 B2
(45) Date of Patent: Dec. 25, 2012

(54) SOFT TISSUE REPAIR DEVICE AND ASSOCIATED METHODS

(75) Inventors: Kevin T. Stone, Winona Lake, IN (US); Ryan A. Kaiser, Leesburg, IN (US); Nathan M. Sautter, North Manchester, IN (US); Andrew Holst, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

(21) Appl. No.: 13/045,689

(22) Filed: Mar. 11, 2011

(65) Prior Publication Data

US 2011/0160767 A1    Jun. 30, 2011

Related U.S. Application Data

(60) Division of application No. 12/014,340, filed on Jan. 15, 2008, now Pat. No. 7,905,904, which is a continuation-in-part of application No. 11/347,661, filed on Feb. 3, 2006, now Pat. No. 7,749,250, and a continuation-in-part of application No. 11/935,681, filed on Nov. 6, 2007, now Pat. No. 7,905,903, and a continuation-in-part of application No. 11/869,440, filed on Oct. 9, 2007, now Pat. No. 7,857,830, which is a continuation-in-part of application No. 11/408,282, filed on Apr. 20, 2006, now abandoned, said application No. 12/014,340 is a continuation-in-part of application No. 11/541,506, filed on Sep. 29, 2006, now Pat. No. 7,601,165.

(60) Provisional application No. 60/885,057, filed on Jan. 16, 2007, provisional application No. 60/885,062, filed on Jan. 16, 2007.

(51) Int. Cl.
*A61B 17/04* (2006.01)

(52) U.S. Cl. ........................................................ 606/232

(58) Field of Classification Search .................. 606/300, 606/213–216, 233, 232, 139; 623/13.11, 623/14.12
See application file for complete search history.

(56) References Cited

U.S. PATENT DOCUMENTS

| | | | |
|---|---|---|---|
| 65,499 A | 6/1867 | Miller |
| 126,366 A | 4/1872 | Wills |
| 233,475 A | 10/1880 | Cook et al. |
| 261,501 A | 7/1882 | Vandermark |
| 268,407 A | 12/1882 | Hughes |
| 417,805 A | 12/1889 | Beaman |

(Continued)

FOREIGN PATENT DOCUMENTS

AU    4957264    3/1966

(Continued)

OTHER PUBLICATIONS

"AperFix® System Surgical Technique Guide. Single Tunnel Double Bundle.™" Cayenne Medical brochure. (Aug. 2008) 8 sheets.

(Continued)

*Primary Examiner* — Dianne Dornbusch
(74) *Attorney, Agent, or Firm* — Harness, Dickey

(57) ABSTRACT

A fibrous tissue repair device includes first and second tubular anchors having corresponding longitudinal passages. The tissue repair device includes corresponding first and second inserters. Each inserter has a shaft with a distal portion received in the longitudinal passage of the corresponding tubular anchor. A flexible strand couples the first and second anchors.

18 Claims, 29 Drawing Sheets

U.S. PATENT DOCUMENTS

| | | | |
|---|---|---|---|
| 487,304 A | 12/1892 | Todd | |
| 762,710 A | 6/1901 | Hall | |
| 837,767 A | 12/1906 | Aims | |
| 838,203 A | 12/1906 | Neil | |
| 1,059,631 A | 4/1913 | Popovics | |
| 1,131,155 A | 3/1915 | Murphy | |
| 1,153,450 A | 9/1915 | Schaff | |
| 1,346,940 A | 7/1920 | Collins | |
| 1,635,066 A | 7/1927 | Wells | |
| 401,677 A | 11/1933 | Hans Albert Roeder | |
| 1,950,799 A | 3/1934 | Jones | |
| 2,065,659 A | 12/1936 | Cullen | |
| 2,108,206 A | 2/1938 | Meeker | |
| 2,121,193 A | 6/1938 | Hanicke | |
| 2,242,003 A | 5/1941 | Lorenzo | |
| 2,267,925 A | 12/1941 | Johnston | |
| 2,302,986 A | 11/1942 | Vollrath | |
| 2,329,398 A | 9/1943 | Duffy | |
| RE22,857 E | 3/1947 | Ogburn | |
| 2,526,959 A | 10/1950 | Lorenzo | |
| 2,528,456 A | 10/1950 | Stevenson | |
| 2,562,419 A | 7/1951 | Ferris | |
| 2,581,564 A | 1/1952 | Villegas | |
| 2,600,395 A | 6/1952 | Domoj et al. | |
| 2,610,631 A | 9/1952 | Calicchio | |
| 2,665,597 A | 1/1954 | Hill | |
| 2,669,774 A | 2/1954 | Mitchell | |
| 2,698,986 A | 1/1955 | Brown | |
| 2,760,488 A | 8/1956 | Pierce | |
| 2,833,284 A | 5/1958 | Springer | |
| 2,846,712 A | 8/1958 | Markman | |
| 2,860,393 A | 11/1958 | Brock | |
| 2,880,728 A | 4/1959 | Rights | |
| 2,881,762 A | 4/1959 | Lowrie | |
| 2,883,096 A | 4/1959 | Dawson | |
| 2,913,042 A | 11/1959 | Taylor | |
| 3,000,009 A | 9/1961 | Selstad | |
| 3,003,155 A | 10/1961 | Mielzynski et al. | |
| 3,013,559 A | 12/1961 | Thomas | |
| 3,037,619 A | 6/1962 | Stevans | |
| 3,039,460 A | 6/1962 | Chandler | |
| 3,090,386 A | 5/1963 | Curtis | |
| 3,103,666 A | 9/1963 | Bone | |
| 3,123,077 A | 3/1964 | Alcamo | |
| 3,125,095 A | 3/1964 | Kaufman et al. | |
| 3,209,422 A | 10/1965 | Dritz | |
| 3,234,938 A | 2/1966 | Robinson | |
| 3,240,379 A | 3/1966 | Bremer et al. | |
| 3,250,271 A | 5/1966 | Lippes | |
| 3,399,432 A | 9/1968 | Merser | |
| 3,409,014 A | 11/1968 | Shannon | |
| RE26,501 E | 12/1968 | Kendrick et al. | |
| 3,435,475 A | 4/1969 | Bisk | |
| 3,467,089 A | 9/1969 | Hasson | |
| 3,470,834 A | 10/1969 | Bone | |
| 3,470,875 A | 10/1969 | Johnson | |
| 3,500,820 A | 3/1970 | Almen | |
| 3,507,274 A | 4/1970 | Soichet | |
| 3,513,484 A | 5/1970 | Hausner | |
| 3,515,132 A | 6/1970 | McKnight | |
| 3,522,803 A | 8/1970 | Majzlin | |
| 3,527,223 A | 9/1970 | Shein | |
| 3,533,406 A | 10/1970 | Hutterer et al. | |
| 3,541,591 A | 11/1970 | Hoegerman | |
| 3,547,389 A | 12/1970 | Mitchell | |
| 3,579,831 A | 5/1971 | Stevens et al. | |
| 3,590,616 A | 7/1971 | Schussler et al. | |
| 3,608,095 A | 9/1971 | Barry | |
| 3,618,447 A | 11/1971 | Goins | |
| 3,628,530 A | 12/1971 | Schwartz | |
| 3,643,649 A | 2/1972 | Amato | |
| 3,648,705 A | 3/1972 | Lary | |
| 3,656,483 A | 4/1972 | Rudel | |
| 3,659,597 A | 5/1972 | Wolfers | |
| 3,664,345 A | 5/1972 | Dabbs et al. | |
| 3,665,560 A | 5/1972 | Bennett et al. | |
| 3,675,639 A | 7/1972 | Cimber | |
| 3,683,422 A | 8/1972 | Stemmer et al. | |
| 3,692,022 A | 9/1972 | Ewing | |
| 3,695,271 A | 10/1972 | Chodorow | |
| 3,699,969 A | 10/1972 | Allen | |
| 3,716,058 A | 2/1973 | Tanner, Jr. | |
| 3,744,488 A | 7/1973 | Cox | |
| 3,752,516 A | 8/1973 | Mumma | |
| 3,757,629 A | 9/1973 | Schneider | |
| 3,763,856 A | 10/1973 | Blomberg | |
| 3,771,520 A | 11/1973 | Lerner | |
| 3,777,748 A | 12/1973 | Abramson | |
| 3,807,407 A | 4/1974 | Schweizer | |
| 3,810,456 A | 5/1974 | Karman | |
| 3,825,010 A | 7/1974 | McDonald | |
| 3,840,017 A | 10/1974 | Violante et al. | |
| 3,842,824 A | 10/1974 | Neufeld | |
| 3,842,840 A | 10/1974 | Schweizer | |
| 3,845,772 A | 11/1974 | Smith | |
| 3,867,933 A | 2/1975 | Kitrilakis | |
| 3,867,944 A | 2/1975 | Samuels | |
| 3,871,368 A | 3/1975 | Johnson et al. | |
| 3,871,379 A | 3/1975 | Clarke | |
| 3,874,388 A | 4/1975 | King et al. | |
| 3,875,648 A | 4/1975 | Bone | |
| 3,877,570 A | 4/1975 | Barry | |
| 3,880,156 A | 4/1975 | Hoff | |
| 3,881,475 A | 5/1975 | Gordon et al. | |
| 3,889,666 A | 6/1975 | Lerner | |
| 3,892,240 A | 7/1975 | Park | |
| 3,896,500 A | 7/1975 | Rambert et al. | |
| 3,907,442 A | 9/1975 | Reid | |
| 3,910,281 A | 10/1975 | Kletschka et al. | |
| 3,918,444 A | 11/1975 | Hoff et al. | |
| 3,918,455 A | 11/1975 | Coplan | |
| 3,927,666 A | 12/1975 | Hoff | |
| 3,931,667 A | 1/1976 | Merser et al. | |
| 3,933,153 A | 1/1976 | Csatary et al. | |
| 3,937,217 A | 2/1976 | Kosonen et al. | |
| 3,943,932 A | 3/1976 | Woo | |
| 3,946,446 A | 3/1976 | Schofield | |
| 3,946,728 A | 3/1976 | Bettex et al. | |
| 3,946,740 A | 3/1976 | Bassett | |
| 3,953,896 A | 5/1976 | Treace | |
| 3,954,103 A | 5/1976 | Garcia-Roel et al. | |
| 3,961,632 A | 6/1976 | Moossun | |
| 3,973,560 A | 8/1976 | Emmett et al. | |
| 3,976,079 A | 8/1976 | Samuels et al. | |
| 3,977,050 A | 8/1976 | Perez et al. | |
| 3,979,799 A | 9/1976 | Merser et al. | |
| 3,985,138 A | 10/1976 | Jarvik | |
| 3,990,619 A | 11/1976 | Russell | |
| 4,005,707 A | 2/1977 | Moulding, Jr. | |
| 4,006,747 A | 2/1977 | Kronenthal et al. | |
| 4,007,743 A | 2/1977 | Blake | |
| 4,013,071 A | 3/1977 | Rosenberg et al. | |
| 4,026,281 A | 5/1977 | Mayberry et al. | |
| 4,036,101 A | 7/1977 | Burnett | |
| 4,050,100 A | 9/1977 | Barry | |
| 4,054,954 A | 10/1977 | Nakayama et al. | |
| 4,085,466 A | 4/1978 | Goodfellow et al. | |
| 4,094,313 A | 6/1978 | Komamura et al. | |
| 4,099,750 A | 7/1978 | McGrew | |
| 4,103,690 A | 8/1978 | Harris | |
| RE29,819 E | 10/1978 | Bone | |
| 4,121,487 A | 10/1978 | Bone | |
| 4,143,656 A | 3/1979 | Holmes et al. | |
| 4,144,876 A | 3/1979 | DeLeo | |
| 4,149,277 A | 4/1979 | Bokros | |
| 4,157,714 A | 6/1979 | Foltz et al. | |
| 4,160,453 A | 7/1979 | Miller | |
| 4,164,225 A | 8/1979 | Johnson et al. | |
| 4,172,458 A | 10/1979 | Pereyra | |
| 4,175,555 A | 11/1979 | Herbert et al. | |
| 4,185,636 A | 1/1980 | Gabbay et al. | |
| 4,196,883 A | 4/1980 | Einhorn et al. | |
| 4,210,148 A | 7/1980 | Stivala | |
| 4,235,161 A | 11/1980 | Kunreuther | |
| 4,235,238 A | 11/1980 | Ogiu et al. | |
| 4,237,779 A | 12/1980 | Kunreuther | |
| 4,243,037 A | 1/1981 | Smith | |

| | | |
|---|---|---|
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A * | 9/1987 | Anderson ............ 606/219 |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,738,255 A | 4/1988 | Goble et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,007,921 A | 4/1991 | Brown |
| 5,030,224 A | 7/1991 | Wright et al. |
| 5,030,235 A | 7/1991 | Campbell, Jr. |
| 5,037,422 A | 8/1991 | Hayhurst |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,074,874 A | 12/1991 | Yoon et al. |

| | | |
|---|---|---|
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,192,282 A | 3/1993 | Draenert et al. |
| 5,197,987 A | 3/1993 | Koch et al. |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,306,301 A | 4/1994 | Graf et al. |
| 5,312,422 A | 5/1994 | Trott |
| 5,312,438 A | 5/1994 | Johnson |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,379,492 A | 1/1995 | Glesser |
| 5,383,878 A | 1/1995 | Roger et al. |
| 5,383,904 A | 1/1995 | Totakura et al. |
| 5,391,171 A | 2/1995 | Schmieding |
| 5,391,176 A | 2/1995 | de la Torre |
| 5,391,182 A * | 2/1995 | Chin ............................ 606/213 |
| 5,393,302 A | 2/1995 | Clark et al. |
| RE34,871 E | 3/1995 | McGuire et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |

| Patent | Date | Inventor | Ref |
|---|---|---|---|
| 5,467,786 A | 11/1995 | Allen et al. | |
| 5,470,334 A | 11/1995 | Ross et al. | |
| 5,470,337 A | 11/1995 | Moss | |
| 5,470,338 A | 11/1995 | Whitfield et al. | |
| 5,472,452 A | 12/1995 | Trott | |
| 5,474,565 A | 12/1995 | Trott | |
| 5,474,568 A | 12/1995 | Scott | |
| 5,474,572 A | 12/1995 | Hayhurst | |
| 5,478,344 A | 12/1995 | Stone et al. | |
| 5,478,345 A | 12/1995 | Stone et al. | |
| 5,480,403 A | 1/1996 | Lee et al. | |
| 5,480,406 A | 1/1996 | Nolan et al. | |
| 5,484,442 A | 1/1996 | Melker et al. | |
| 5,486,197 A | 1/1996 | Le et al. | |
| 5,490,750 A | 2/1996 | Gundy | |
| 5,496,331 A | 3/1996 | Xu et al. | |
| 5,496,348 A | 3/1996 | Bonutti | |
| 5,500,000 A | 3/1996 | Feagin et al. | |
| 5,505,736 A | 4/1996 | Reimels et al. | |
| 5,507,754 A | 4/1996 | Green et al. | |
| 5,520,691 A | 5/1996 | Branch | |
| 5,520,700 A * | 5/1996 | Beyar et al. | 606/139 |
| 5,520,702 A | 5/1996 | Sauer et al. | |
| 5,522,817 A | 6/1996 | Sander et al. | |
| 5,522,820 A | 6/1996 | Caspari et al. | |
| 5,522,844 A | 6/1996 | Johnson | |
| 5,522,845 A | 6/1996 | Wenstrom, Jr. | |
| 5,522,846 A | 6/1996 | Bonutti | |
| 5,524,946 A | 6/1996 | Thompson | |
| 5,527,321 A | 6/1996 | Hinchliffe | |
| 5,527,342 A | 6/1996 | Pietrzak et al. | |
| 5,527,343 A | 6/1996 | Bonutti | |
| 5,534,012 A | 7/1996 | Bonutti | |
| 5,536,270 A | 7/1996 | Songer et al. | |
| 5,540,698 A | 7/1996 | Preissman | |
| 5,540,703 A | 7/1996 | Barker, Jr. et al. | |
| 5,540,718 A * | 7/1996 | Bartlett | 606/232 |
| 5,545,168 A | 8/1996 | Burke | |
| 5,545,178 A | 8/1996 | Kensey et al. | |
| 5,545,180 A | 8/1996 | Le et al. | |
| 5,545,228 A | 8/1996 | Kambin | |
| 5,549,613 A | 8/1996 | Goble et al. | |
| 5,549,617 A | 8/1996 | Green et al. | |
| 5,549,619 A | 8/1996 | Peters et al. | |
| 5,549,630 A | 8/1996 | Bonutti | |
| 5,549,631 A | 8/1996 | Bonutti | |
| 5,562,683 A | 10/1996 | Chan | |
| 5,562,685 A | 10/1996 | Mollenauer et al. | |
| 5,562,686 A | 10/1996 | Sauer et al. | |
| 5,569,269 A | 10/1996 | Hart et al. | |
| 5,569,305 A | 10/1996 | Bonutti | |
| 5,571,090 A | 11/1996 | Sherts | |
| 5,571,139 A | 11/1996 | Jenkins, Jr. | |
| 5,572,655 A | 11/1996 | Tuljapurkar et al. | |
| 5,573,286 A | 11/1996 | Rogozinski | |
| 5,573,542 A | 11/1996 | Stevens | |
| 5,573,548 A | 11/1996 | Nazre et al. | |
| 5,577,299 A | 11/1996 | Thompson et al. | |
| 5,578,057 A | 11/1996 | Wenstrom, Jr. | |
| 5,584,695 A | 12/1996 | Lal Sachdeva et al. | |
| 5,584,835 A | 12/1996 | Greenfield | |
| 5,584,836 A | 12/1996 | Ballintyn et al. | |
| 5,584,862 A | 12/1996 | Bonutti | |
| 5,586,986 A | 12/1996 | Hinchliffe | |
| 5,588,575 A | 12/1996 | Davignon | |
| 5,591,180 A | 1/1997 | Hinchliffe | |
| 5,591,181 A | 1/1997 | Stone et al. | |
| 5,591,207 A | 1/1997 | Coleman | |
| 5,593,407 A | 1/1997 | Reis et al. | |
| 5,593,425 A | 1/1997 | Bonutti et al. | |
| 5,601,557 A | 2/1997 | Hayhurst | |
| 5,601,559 A | 2/1997 | Melker et al. | |
| 5,601,571 A | 2/1997 | Moss | |
| 5,603,716 A | 2/1997 | Morgan et al. | |
| 5,607,429 A | 3/1997 | Hayano et al. | |
| 5,618,290 A | 4/1997 | Toy et al. | |
| 5,626,611 A | 5/1997 | Liu et al. | |
| 5,626,614 A * | 5/1997 | Hart | 606/232 |
| 5,628,756 A | 5/1997 | Barker, Jr. et al. | |
| 5,628,766 A | 5/1997 | Johnson | |
| 5,630,824 A | 5/1997 | Hart | |
| 5,632,748 A | 5/1997 | Beck, Jr. et al. | |
| 5,641,256 A | 6/1997 | Gundy | |
| 5,643,266 A | 7/1997 | Li | |
| 5,643,269 A | 7/1997 | Harle et al. | |
| 5,643,295 A | 7/1997 | Yoon | |
| 5,643,319 A * | 7/1997 | Green et al. | 606/218 |
| 5,643,320 A | 7/1997 | Lower et al. | |
| 5,643,321 A | 7/1997 | McDevitt | |
| 5,645,546 A | 7/1997 | Fard | |
| 5,645,547 A | 7/1997 | Coleman | |
| 5,645,568 A | 7/1997 | Chervitz et al. | |
| 5,645,588 A | 7/1997 | Graf et al. | |
| 5,647,874 A | 7/1997 | Hayhurst | |
| 5,649,959 A | 7/1997 | Hannam et al. | |
| 5,649,963 A | 7/1997 | McDevitt | |
| 5,658,289 A | 8/1997 | Boucher et al. | |
| 5,658,299 A | 8/1997 | Hart | |
| 5,658,313 A | 8/1997 | Thal | |
| 5,662,658 A | 9/1997 | Wenstrom, Jr. | |
| 5,662,663 A | 9/1997 | Shallman | |
| 5,665,112 A | 9/1997 | Thal | |
| 5,667,513 A | 9/1997 | Torrie et al. | |
| 5,671,695 A | 9/1997 | Schroeder | |
| 5,674,224 A | 10/1997 | Howell et al. | |
| 5,679,723 A | 10/1997 | Cooper et al. | |
| 5,681,334 A | 10/1997 | Evans et al. | |
| 5,681,352 A | 10/1997 | Clancy, III et al. | |
| 5,683,419 A | 11/1997 | Thal | |
| 5,688,285 A | 11/1997 | Yamada et al. | |
| 5,690,676 A | 11/1997 | DiPoto et al. | |
| 5,690,678 A | 11/1997 | Johnson | |
| 5,693,046 A | 12/1997 | Songer et al. | |
| 5,695,497 A | 12/1997 | Stahelin et al. | |
| 5,697,929 A | 12/1997 | Mellinger | |
| 5,699,657 A | 12/1997 | Paulson | |
| 5,702,397 A | 12/1997 | Goble et al. | |
| 5,702,422 A | 12/1997 | Stone | |
| 5,702,462 A | 12/1997 | Oberlander | |
| 5,707,373 A | 1/1998 | Sevrain et al. | |
| 5,711,969 A | 1/1998 | Patel et al. | |
| 5,713,005 A | 1/1998 | Proebsting | |
| 5,713,904 A | 2/1998 | Errico et al. | |
| 5,713,905 A | 2/1998 | Goble et al. | |
| 5,713,921 A | 2/1998 | Bonutti | |
| 5,716,359 A | 2/1998 | Ojima et al. | |
| 5,716,397 A | 2/1998 | Myers | |
| 5,718,717 A | 2/1998 | Bonutti | |
| 5,720,747 A | 2/1998 | Burke | |
| 5,720,765 A | 2/1998 | Thal | |
| 5,720,766 A | 2/1998 | Zang et al. | |
| 5,722,976 A | 3/1998 | Brown | |
| 5,725,549 A | 3/1998 | Lam | |
| 5,725,556 A | 3/1998 | Moser et al. | |
| 5,725,581 A | 3/1998 | Br.ang.nemark et al. | |
| 5,725,582 A | 3/1998 | Bevan et al. | |
| 5,726,722 A | 3/1998 | Uehara et al. | |
| 5,728,107 A | 3/1998 | Zlock et al. | |
| 5,728,109 A | 3/1998 | Schulze et al. | |
| 5,728,136 A | 3/1998 | Thal | |
| 5,733,293 A | 3/1998 | Scirica et al. | |
| 5,733,306 A | 3/1998 | Bonutti | |
| 5,733,307 A | 3/1998 | Dinsdale | |
| 5,735,875 A | 4/1998 | Bonutti et al. | |
| 5,741,259 A | 4/1998 | Chan | |
| 5,741,260 A | 4/1998 | Songer et al. | |
| 5,741,281 A | 4/1998 | Martin et al. | |
| 5,743,912 A | 4/1998 | Lahille et al. | |
| 5,746,751 A | 5/1998 | Sherts | |
| 5,746,752 A | 5/1998 | Burkhart | |
| 5,746,754 A | 5/1998 | Chan | |
| 5,749,898 A | 5/1998 | Schulze et al. | |
| 5,755,729 A | 5/1998 | de la Torre et al. | |
| 5,755,791 A | 5/1998 | Whitson et al. | |
| 5,766,176 A | 6/1998 | Duncan | |
| 5,766,218 A | 6/1998 | Arnott | |
| 5,766,250 A | 6/1998 | Chervitz et al. | |
| 5,769,894 A | 6/1998 | Ferragamo | |

| | | | | | | |
|---|---|---|---|---|---|---|
| 5,769,899 A | 6/1998 | Schwartz et al. | | 5,968,047 A | 10/1999 | Reed |
| 5,772,673 A | 6/1998 | Cuny et al. | | 5,968,077 A | 10/1999 | Wojciechowicz et al. |
| 5,776,196 A | 7/1998 | Matsuzaki et al. | | 5,972,006 A | 10/1999 | Sciaino, Jr. |
| 5,782,845 A * | 7/1998 | Shewchuk ............... 606/144 | | 5,976,125 A | 11/1999 | Graham |
| 5,782,862 A | 7/1998 | Bonutti | | 5,976,127 A | 11/1999 | Lax |
| 5,782,864 A | 7/1998 | Lizardi | | 5,980,524 A | 11/1999 | Justin et al. |
| 5,782,866 A | 7/1998 | Wenstrom, Jr. | | 5,980,539 A | 11/1999 | Kontos |
| 5,785,714 A | 7/1998 | Morgan et al. | | 5,980,558 A | 11/1999 | Wiley |
| 5,792,142 A | 8/1998 | Galitzer | | 5,980,559 A | 11/1999 | Bonutti |
| 5,792,149 A | 8/1998 | Sherts et al. | | 5,989,252 A | 11/1999 | Fumex |
| 5,796,127 A | 8/1998 | Hayafuji et al. | | 5,989,256 A | 11/1999 | Kuslich et al. |
| 5,797,915 A | 8/1998 | Pierson, III et al. | | 5,989,282 A | 11/1999 | Bonutti |
| 5,797,928 A | 8/1998 | Kogasaka | | 5,993,452 A | 11/1999 | Vandewalle |
| 5,800,407 A | 9/1998 | Eldor et al. | | 5,993,476 A | 11/1999 | Groiso |
| 5,810,824 A | 9/1998 | Chan | | 5,997,542 A | 12/1999 | Burke |
| 5,810,848 A | 9/1998 | Hayhurst | | 5,997,552 A | 12/1999 | Person et al. |
| 5,814,069 A | 9/1998 | Schulze et al. | | 5,997,575 A | 12/1999 | Whitson et al. |
| 5,814,070 A | 9/1998 | Borzone et al. | | 6,001,100 A | 12/1999 | Sherman et al. |
| 5,814,072 A | 9/1998 | Bonutti | | 6,007,538 A | 12/1999 | Levin |
| 5,814,073 A | 9/1998 | Bonutti | | 6,007,567 A | 12/1999 | Bonutti |
| 5,823,980 A | 10/1998 | Kopfer | | 6,010,525 A | 1/2000 | Bonutti et al. |
| 5,824,011 A | 10/1998 | Stone et al. | | 6,016,727 A | 1/2000 | Morgan |
| 5,830,234 A | 11/1998 | Wojciechowicz et al. | | 6,022,352 A | 2/2000 | Vandewalle |
| 5,843,084 A | 12/1998 | Hart et al. | | 6,022,373 A | 2/2000 | Li |
| 5,845,645 A | 12/1998 | Bonutti | | 6,024,758 A | 2/2000 | Thal |
| 5,846,254 A | 12/1998 | Schulze et al. | | 6,027,523 A | 2/2000 | Schmieding |
| 5,848,983 A | 12/1998 | Basaj et al. | | 6,030,410 A | 2/2000 | Zurbrugg |
| 5,849,012 A | 12/1998 | Abboudi | | 6,033,429 A | 3/2000 | Magovern |
| 5,860,973 A | 1/1999 | Michelson | | 6,033,430 A | 3/2000 | Bonutti |
| 5,868,740 A | 2/1999 | LeVeen et al. | | 6,039,753 A | 3/2000 | Meislin |
| 5,868,748 A | 2/1999 | Burke | | 6,041,485 A | 3/2000 | Pedlick et al. |
| 5,868,789 A | 2/1999 | Huebner | | 6,042,601 A | 3/2000 | Smith |
| 5,871,484 A | 2/1999 | Spievack et al. | | 6,045,551 A | 4/2000 | Bonutti |
| 5,871,486 A | 2/1999 | Huebner et al. | | 6,045,571 A | 4/2000 | Hill et al. |
| 5,871,490 A | 2/1999 | Schulze et al. | | 6,045,572 A | 4/2000 | Johnson et al. |
| 5,885,294 A | 3/1999 | Pedlick et al. | | 6,045,573 A | 4/2000 | Wenstrom, Jr. et al. |
| 5,891,168 A | 4/1999 | Thal | | 6,045,574 A | 4/2000 | Thal |
| 5,893,592 A | 4/1999 | Schulze et al. | | 6,047,826 A | 4/2000 | Kalinski et al. |
| 5,895,395 A | 4/1999 | Yeung | | 6,048,343 A | 4/2000 | Mathis et al. |
| 5,897,564 A | 4/1999 | Schulze et al. | | 6,051,006 A | 4/2000 | Shluzas et al. |
| 5,897,574 A | 4/1999 | Bonutti | | 6,051,007 A | 4/2000 | Hogendijk et al. |
| 5,899,902 A | 5/1999 | Brown et al. | | 6,053,916 A | 4/2000 | Moore |
| 5,899,938 A | 5/1999 | Sklar et al. | | 6,053,921 A | 4/2000 | Wagner et al. |
| 5,908,421 A | 6/1999 | Beger et al. | | 6,056,752 A | 5/2000 | Roger |
| 5,908,436 A | 6/1999 | Cuschieri et al. | | 6,056,772 A | 5/2000 | Bonutti |
| 5,910,148 A | 6/1999 | Reimels et al. | | 6,056,773 A | 5/2000 | Bonutti |
| 5,911,721 A | 6/1999 | Nicholson et al. | | 6,059,817 A | 5/2000 | Bonutti et al. |
| 5,918,604 A | 7/1999 | Whelan | | 6,059,818 A | 5/2000 | Johnson et al. |
| 5,921,986 A | 7/1999 | Bonutti | | 6,062,344 A | 5/2000 | Okabe et al. |
| 5,925,008 A | 7/1999 | Douglas | | 6,068,648 A | 5/2000 | Cole et al. |
| 5,928,231 A | 7/1999 | Klein et al. | | 6,071,305 A | 6/2000 | Brown et al. |
| 5,928,267 A | 7/1999 | Bonutti et al. | | 6,074,403 A | 6/2000 | Nord |
| RE36,289 E | 8/1999 | Le et al. | | 6,077,277 A | 6/2000 | Mollenauer et al. |
| 5,931,838 A | 8/1999 | Vito | | 6,077,292 A | 6/2000 | Bonutti |
| 5,931,844 A | 8/1999 | Thompson et al. | | 6,080,185 A | 6/2000 | Johnson et al. |
| 5,931,869 A | 8/1999 | Boucher et al. | | 6,086,591 A | 7/2000 | Bojarski |
| 5,935,119 A | 8/1999 | Guy et al. | | 6,086,592 A | 7/2000 | Rosenberg et al. |
| 5,935,133 A | 8/1999 | Wagner et al. | | 6,086,608 A | 7/2000 | Ek et al. |
| 5,935,149 A | 8/1999 | Ek | | 6,093,200 A | 7/2000 | Liu et al. |
| 5,938,668 A | 8/1999 | Scirica et al. | | 6,096,060 A | 8/2000 | Fitts et al. |
| 5,941,439 A | 8/1999 | Kammerer et al. | | 6,099,527 A | 8/2000 | Hochschuler et al. |
| 5,941,900 A | 8/1999 | Bonutti | | 6,099,530 A | 8/2000 | Simonian et al. |
| 5,944,739 A | 8/1999 | Zlock et al. | | 6,099,568 A | 8/2000 | Simonian et al. |
| 5,946,783 A | 9/1999 | Plociennik et al. | | 6,106,545 A | 8/2000 | Egan |
| 5,947,915 A | 9/1999 | Thibodo, Jr. | | 6,110,128 A | 8/2000 | Andelin et al. |
| 5,947,982 A | 9/1999 | Duran | | 6,117,160 A | 9/2000 | Bonutti |
| 5,947,999 A | 9/1999 | Groiso | | 6,117,162 A | 9/2000 | Schmieding et al. |
| 5,948,002 A | 9/1999 | Bonutti | | 6,123,710 A | 9/2000 | Pinczewski et al. |
| 5,951,559 A | 9/1999 | Burkhart | | 6,132,433 A | 10/2000 | Whelan |
| 5,951,560 A | 9/1999 | Simon et al. | | 6,132,437 A | 10/2000 | Omurtag et al. |
| 5,954,747 A | 9/1999 | Clark | | 6,139,565 A | 10/2000 | Stone et al. |
| 5,957,953 A | 9/1999 | DiPoto et al. | | RE36,974 E | 11/2000 | Bonutti |
| 5,961,521 A | 10/1999 | Roger et al. | | 6,143,017 A | 11/2000 | Thal |
| 5,961,524 A | 10/1999 | Crombie | | 6,146,406 A | 11/2000 | Shluzas et al. |
| 5,964,764 A | 10/1999 | West, Jr. et al. | | 6,146,408 A | 11/2000 | Bartlett |
| 5,964,767 A | 10/1999 | Tapia et al. | | 6,149,653 A | 11/2000 | Deslauriers |
| 5,964,769 A | 10/1999 | Wagner et al. | | 6,149,669 A * | 11/2000 | Li ............... 606/232 |
| 5,964,783 A | 10/1999 | Grafton et al. | | 6,152,928 A | 11/2000 | Wenstrom, Jr. |
| 5,968,045 A | 10/1999 | Frazier | | 6,152,934 A | 11/2000 | Harper et al. |

| | | | |
|---|---|---|---|
| 6,152,936 A | 11/2000 | Christy et al. | |
| 6,152,949 A | 11/2000 | Bonutti | |
| 6,156,039 A | 12/2000 | Thal | |
| 6,156,056 A | 12/2000 | Kearns et al. | |
| 6,159,234 A | 12/2000 | Bonutti et al. | |
| 6,165,203 A | 12/2000 | Krebs | |
| 6,168,598 B1 | 1/2001 | Martello | |
| 6,168,628 B1 | 1/2001 | Huebner | |
| 6,179,840 B1 | 1/2001 | Bowman | |
| 6,183,461 B1 | 2/2001 | Matsuura et al. | |
| 6,187,025 B1 | 2/2001 | Machek | |
| 6,190,401 B1 | 2/2001 | Green et al. | |
| 6,190,411 B1 | 2/2001 | Lo et al. | |
| 6,193,754 B1 | 2/2001 | Seedhom | |
| 6,200,318 B1 | 3/2001 | Har-Shai et al. | |
| 6,200,329 B1 | 3/2001 | Fung et al. | |
| 6,200,330 B1 | 3/2001 | Benderev et al. | |
| 6,203,556 B1 | 3/2001 | Evans et al. | |
| 6,203,565 B1 | 3/2001 | Bonutti et al. | |
| 6,203,572 B1 | 3/2001 | Johnson et al. | |
| 6,206,883 B1 | 3/2001 | Tunc | |
| 6,210,376 B1 | 4/2001 | Grayson | |
| 6,214,012 B1 | 4/2001 | Karpman et al. | |
| 6,217,580 B1 | 4/2001 | Levin | |
| 6,221,107 B1 | 4/2001 | Steiner et al. | |
| 6,228,096 B1 | 5/2001 | Marchand | |
| 6,231,592 B1 | 5/2001 | Bonutti et al. | |
| 6,235,057 B1 | 5/2001 | Roger et al. | |
| 6,238,395 B1 | 5/2001 | Bonutti | |
| 6,241,734 B1 | 6/2001 | Scribner et al. | |
| 6,241,747 B1 | 6/2001 | Ruff | |
| 6,241,771 B1 | 6/2001 | Gresser et al. | |
| 6,245,081 B1 | 6/2001 | Bowman et al. | |
| 6,258,091 B1 | 7/2001 | Sevrain et al. | |
| 6,267,766 B1 | 7/2001 | Burkhart | |
| 6,269,716 B1 | 8/2001 | Amis | |
| 6,270,518 B1 | 8/2001 | Pedlick et al. | |
| 6,273,890 B1 | 8/2001 | Frazier | |
| 6,283,973 B1 | 9/2001 | Hubbard et al. | |
| 6,283,996 B1 | 9/2001 | Chervitz et al. | |
| 6,287,307 B1 | 9/2001 | Abboudi | |
| 6,287,325 B1 | 9/2001 | Bonutti | |
| 6,293,961 B2 | 9/2001 | Schwartz et al. | |
| 6,296,659 B1 | 10/2001 | Foerster | |
| 6,299,615 B1 | 10/2001 | Huebner | |
| 6,302,888 B1 | 10/2001 | Mellinger et al. | |
| 6,302,899 B1 | 10/2001 | Johnson et al. | |
| 6,306,156 B1 | 10/2001 | Clark | |
| 6,306,159 B1 | 10/2001 | Schwartz et al. | |
| 6,309,405 B1 | 10/2001 | Bonutti | |
| 6,312,448 B1 | 11/2001 | Bonutti | |
| 6,315,788 B1 | 11/2001 | Roby | |
| 6,319,271 B1 | 11/2001 | Schwartz et al. | |
| 6,328,758 B1 | 12/2001 | Tornier et al. | |
| 6,342,060 B1 | 1/2002 | Adams | |
| 6,343,531 B2 | 2/2002 | Amis | |
| 6,358,270 B1 | 3/2002 | Lemer | |
| 6,364,897 B1 | 4/2002 | Bonutti | |
| 6,368,322 B1 | 4/2002 | Luks et al. | |
| 6,368,326 B1 | 4/2002 | Dakin et al. | |
| 6,368,343 B1 | 4/2002 | Bonutti et al. | |
| 6,371,124 B1 | 4/2002 | Whelan | |
| 6,379,361 B1 | 4/2002 | Beck, Jr. et al. | |
| 6,383,190 B1 | 5/2002 | Preissman | |
| 6,383,199 B2 | 5/2002 | Carter et al. | |
| 6,387,113 B1 | 5/2002 | Hawkins et al. | |
| 6,387,129 B2 | 5/2002 | Rieser et al. | |
| 6,391,030 B1 | 5/2002 | Wagner et al. | |
| 6,398,785 B2 | 6/2002 | Carchidi et al. | |
| 6,406,479 B1 | 6/2002 | Justin et al. | |
| 6,409,743 B1 | 6/2002 | Fenton, Jr. | |
| 6,413,260 B1 | 7/2002 | Berrevoets et al. | |
| 6,423,088 B1 | 7/2002 | Fenton, Jr. | |
| 6,428,562 B2 | 8/2002 | Bonutti | |
| 6,432,123 B2 | 8/2002 | Schwartz et al. | |
| 6,436,123 B1 | 8/2002 | Magovern | |
| 6,436,124 B1 | 8/2002 | Anderson et al. | |
| 6,440,134 B1 | 8/2002 | Zaccherotti et al. | |
| 6,440,136 B1 | 8/2002 | Gambale et al. | |
| 6,447,516 B1 | 9/2002 | Bonutti | |
| 6,451,030 B1 | 9/2002 | Li et al. | |
| 6,454,768 B1 | 9/2002 | Jackson | |
| 6,458,134 B1 | 10/2002 | Songer et al. | |
| 6,461,373 B2 | 10/2002 | Wyman et al. | |
| 6,464,713 B2 | 10/2002 | Bonutti | |
| 6,468,293 B2 | 10/2002 | Bonutti et al. | |
| 6,471,707 B1 | 10/2002 | Miller et al. | |
| 6,475,230 B1 | 11/2002 | Bonutti et al. | |
| 6,482,210 B1 | 11/2002 | Skiba et al. | |
| 6,485,504 B1 | 11/2002 | Johnson et al. | |
| 6,497,901 B1 | 12/2002 | Royer | |
| 6,500,184 B1 * | 12/2002 | Chan et al. | 606/144 |
| 6,500,195 B2 | 12/2002 | Bonutti | |
| RE37,963 E | 1/2003 | Thal | |
| 6,503,267 B2 | 1/2003 | Bonutti et al. | |
| 6,506,190 B1 | 1/2003 | Walshe | |
| 6,508,820 B2 | 1/2003 | Bales | |
| 6,508,821 B1 | 1/2003 | Schwartz et al. | |
| 6,508,830 B2 | 1/2003 | Steiner | |
| 6,511,498 B1 | 1/2003 | Fumex | |
| 6,511,499 B2 | 1/2003 | Schmieding et al. | |
| 6,517,542 B1 | 2/2003 | Papay et al. | |
| 6,517,552 B1 | 2/2003 | Nord et al. | |
| 6,517,578 B2 | 2/2003 | Hein | |
| 6,517,579 B1 | 2/2003 | Paulos et al. | |
| 6,520,964 B2 | 2/2003 | Tallarida et al. | |
| 6,520,980 B1 | 2/2003 | Foerster | |
| 6,524,317 B1 | 2/2003 | Ritchart et al. | |
| 6,527,777 B2 | 3/2003 | Justin | |
| 6,527,794 B1 | 3/2003 | McDevitt et al. | |
| 6,527,795 B1 | 3/2003 | Lizardi | |
| 6,533,795 B1 | 3/2003 | Tran et al. | |
| 6,533,802 B2 | 3/2003 | Bojarski et al. | |
| 6,537,319 B2 | 3/2003 | Whelan | |
| 6,540,750 B2 | 4/2003 | Burkhart | |
| 6,540,769 B1 | 4/2003 | Miller, III | |
| 6,540,770 B1 | 4/2003 | Tornier et al. | |
| 6,544,281 B2 | 4/2003 | ElAttrache et al. | |
| 6,547,564 B1 | 4/2003 | Hansson | |
| 6,547,778 B1 | 4/2003 | Sklar et al. | |
| 6,547,800 B2 | 4/2003 | Foerster et al. | |
| 6,551,330 B1 | 4/2003 | Bain et al. | |
| 6,551,343 B1 | 4/2003 | Tormala et al. | |
| 6,553,802 B1 | 4/2003 | Jacob et al. | |
| 6,554,830 B1 | 4/2003 | Chappius | |
| 6,554,852 B1 * | 4/2003 | Oberlander | 606/232 |
| 6,554,862 B2 | 4/2003 | Hays et al. | |
| 6,562,071 B2 | 5/2003 | Jarvinen et al. | |
| 6,565,572 B2 | 5/2003 | Chappius | |
| 6,565,573 B1 | 5/2003 | Ferrante et al. | |
| 6,569,186 B1 | 5/2003 | Winters et al. | |
| 6,569,187 B1 | 5/2003 | Bonutti et al. | |
| 6,572,635 B1 | 6/2003 | Bonutti | |
| 6,575,925 B1 | 6/2003 | Noble | |
| 6,579,295 B1 | 6/2003 | Supinski | |
| 6,582,453 B1 | 6/2003 | Tran et al. | |
| 6,585,730 B1 | 7/2003 | Foerster | |
| 6,585,740 B2 | 7/2003 | Schlapfer et al. | |
| 6,585,750 B2 | 7/2003 | Bonutti et al. | |
| 6,589,245 B1 | 7/2003 | Weiler et al. | |
| 6,589,246 B1 | 7/2003 | Hack et al. | |
| 6,592,609 B1 | 7/2003 | Bonutti | |
| 6,595,911 B2 | 7/2003 | LoVuolo | |
| 6,599,289 B1 | 7/2003 | Bojarski et al. | |
| 6,599,319 B2 | 7/2003 | Knudsen et al. | |
| 6,605,096 B1 | 8/2003 | Ritchart | |
| 6,607,548 B2 | 8/2003 | Pohjonen et al. | |
| 6,610,079 B1 | 8/2003 | Li et al. | |
| 6,613,018 B2 | 9/2003 | Bagga et al. | |
| 6,616,694 B1 | 9/2003 | Hart | |
| 6,620,166 B1 | 9/2003 | Wenstrom, Jr. et al. | |
| 6,620,185 B1 | 9/2003 | Harvie et al. | |
| 6,620,195 B2 | 9/2003 | Goble et al. | |
| 6,620,329 B2 | 9/2003 | Rosen et al. | |
| 6,620,349 B1 | 9/2003 | Lopez | |
| 6,623,492 B1 | 9/2003 | Berube et al. | |
| 6,623,524 B2 | 9/2003 | Schmieding | |
| 6,626,910 B1 | 9/2003 | Hugues et al. | |

| | | |
|---|---|---|
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,450 B2 | 11/2003 | Neisz et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,966,887 B1 | 11/2005 | Chin |
| 6,966,916 B2 * | 11/2005 | Kumar .................. 606/144 |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 7,001,429 B2 | 2/2006 | Ferguson |
| 7,004,959 B2 | 2/2006 | Bonutti |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 * | 8/2006 | Hyde .................. 606/142 |
| 7,105,010 B2 | 9/2006 | Hart et al. |
| 7,112,221 B2 | 9/2006 | Harris et al. |
| 7,118,583 B2 | 10/2006 | O'Quinn et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,333 B2 | 1/2007 | Plouhar et al. |
| 7,201,722 B2 | 4/2007 | Krueger |
| 7,255,675 B2 | 8/2007 | Gertner et al. |
| 7,255,715 B2 | 8/2007 | Metzger |
| 7,261,716 B2 | 8/2007 | Strobel et al. |
| 7,264,634 B2 | 9/2007 | Schmieding |
| 7,285,124 B2 | 10/2007 | Foerster |
| 7,303,577 B1 | 12/2007 | Dean |
| 7,306,417 B2 | 12/2007 | Dorstewitz |
| 7,326,222 B2 | 2/2008 | Dreyfuss et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,494,506 B2 | 2/2009 | Brulez et al. |
| 7,513,910 B2 | 4/2009 | Buskirk et al. |
| 7,578,825 B2 | 8/2009 | Huebner |
| 7,585,311 B2 | 9/2009 | Green et al. |
| 7,601,165 B2 | 10/2009 | Stone |
| 7,608,098 B1 | 10/2009 | Stone et al. |
| 7,615,076 B2 | 11/2009 | Cauthen, III et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,736,379 B2 | 6/2010 | Ewers et al. |
| 7,758,594 B2 | 7/2010 | Lamson et al. |
| 7,776,041 B1 | 8/2010 | Walters |
| 7,819,895 B2 | 10/2010 | Ginn et al. |
| 7,875,058 B2 | 1/2011 | Holmes, Jr. |
| 7,981,140 B2 | 7/2011 | Burkhart |
| 8,062,334 B2 | 11/2011 | Green et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0037131 A1 | 11/2001 | Schmieding et al. |
| 2001/0037153 A1 | 11/2001 | Rockwood et al. |
| 2001/0041916 A1 * | 11/2001 | Bonutti .................. 606/232 |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |

| | | |
|---|---|---|
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2002/0193830 A1 | 12/2002 | Bonutti |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1* | 6/2003 | Eichhorn et al. ............ 606/232 |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1* | 9/2003 | Oberlander ............... 606/232 |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1* | 7/2004 | Shelton et al. ............ 606/151 |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243235 A1 | 12/2004 | Goh et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |

| | | | | | |
|---|---|---|---|---|---|
| 2005/0283158 A1 | 12/2005 | West | 2008/0027446 A1 | 1/2008 | Stone et al. |
| 2005/0283192 A1 | 12/2005 | Torrie et al. | 2008/0046009 A1 | 2/2008 | Albertorio et al. |
| 2006/0004410 A1 | 1/2006 | Nobis et al. | 2008/0065114 A1 | 3/2008 | Stone et al. |
| 2006/0015103 A1 | 1/2006 | Burke | 2008/0071299 A1 | 3/2008 | Allinniemi et al. |
| 2006/0015106 A1 | 1/2006 | Lerch et al. | 2008/0082101 A1 | 4/2008 | Reisberg |
| 2006/0030884 A1* | 2/2006 | Yeung et al. ............ 606/232 | 2008/0082127 A1 | 4/2008 | Stone et al. |
| 2006/0030948 A1 | 2/2006 | Manrique et al. | 2008/0082128 A1 | 4/2008 | Stone |
| 2006/0036265 A1 | 2/2006 | Dant | 2008/0119892 A1 | 5/2008 | Brailovski et al. |
| 2006/0052818 A1 | 3/2006 | Drake et al. | 2008/0132753 A1 | 6/2008 | Goddard |
| 2006/0064125 A1 | 3/2006 | Henderson et al. | 2008/0132932 A1 | 6/2008 | Hoeppner et al. |
| 2006/0064126 A1 | 3/2006 | Fallin et al. | 2008/0140092 A1 | 6/2008 | Stone et al. |
| 2006/0069334 A1 | 3/2006 | Moskowitz | 2008/0140093 A1 | 6/2008 | Stone et al. |
| 2006/0084943 A1 | 4/2006 | Rosenman et al. | 2008/0140128 A1 | 6/2008 | Smisson et al. |
| 2006/0085000 A1 | 4/2006 | Mohr et al. | 2008/0161852 A1 | 7/2008 | Kaiser et al. |
| 2006/0089672 A1 | 4/2006 | Martinek | 2008/0161861 A1 | 7/2008 | Huebner |
| 2006/0100627 A1 | 5/2006 | Stone et al. | 2008/0172097 A1 | 7/2008 | Lerch et al. |
| 2006/0100637 A1 | 5/2006 | Rathbun et al. | 2008/0188933 A1 | 8/2008 | Koob et al. |
| 2006/0111721 A1 | 5/2006 | Puricelli et al. | 2008/0188936 A1 | 8/2008 | Ball et al. |
| 2006/0116685 A1 | 6/2006 | Urbanski et al. | 2008/0221527 A1 | 9/2008 | Bradley et al. |
| 2006/0121084 A1 | 6/2006 | Borden et al. | 2008/0221578 A1 | 9/2008 | Zeitani |
| 2006/0122611 A1 | 6/2006 | Morales et al. | 2008/0255613 A1 | 10/2008 | Kaiser et al. |
| 2006/0135958 A1 | 6/2006 | Marissen et al. | 2008/0262544 A1 | 10/2008 | Burkhart |
| 2006/0149266 A1 | 7/2006 | Cordasco | 2008/0268064 A1 | 10/2008 | Woodell-May |
| 2006/0161161 A1 | 7/2006 | Shifrin et al. | 2008/0269674 A1 | 10/2008 | Stone |
| 2006/0167458 A1 | 7/2006 | Gabele | 2008/0275477 A1 | 11/2008 | Sterrett et al. |
| 2006/0167481 A1 | 7/2006 | Baker et al. | 2008/0312689 A1 | 12/2008 | Denham et al. |
| 2006/0167482 A1 | 7/2006 | Swain et al. | 2009/0018589 A1 | 1/2009 | Smisson, III et al. |
| 2006/0173492 A1 | 8/2006 | Akerfeldt et al. | 2009/0018655 A1 | 1/2009 | Brunelle et al. |
| 2006/0178680 A1 | 8/2006 | Nelson et al. | 2009/0054928 A1 | 2/2009 | Denham et al. |
| 2006/0189993 A1 | 8/2006 | Stone | 2009/0062854 A1 | 3/2009 | Kaiser et al. |
| 2006/0190042 A1 | 8/2006 | Stone et al. | 2009/0082790 A1 | 3/2009 | Shad et al. |
| 2006/0195101 A1 | 8/2006 | Stevens | 2009/0082805 A1 | 3/2009 | Kaiser et al. |
| 2006/0200235 A1 | 9/2006 | Bianchi et al. | 2009/0099598 A1 | 4/2009 | McDevitt et al. |
| 2006/0229671 A1 | 10/2006 | Steiner et al. | 2009/0105754 A1 | 4/2009 | Sethi |
| 2006/0235407 A1 | 10/2006 | Wang et al. | 2009/0118774 A1 | 5/2009 | Miller III |
| 2006/0241624 A1 | 10/2006 | Kizuka et al. | 2009/0118775 A1 | 5/2009 | Burke |
| 2006/0247642 A1 | 11/2006 | Stone et al. | 2009/0125073 A1 | 5/2009 | Rehm |
| 2006/0253130 A1 | 11/2006 | Wolniewicz | 2009/0138002 A1 | 5/2009 | Fenton |
| 2006/0259048 A1 | 11/2006 | Koseki | 2009/0138054 A1 | 5/2009 | Teague et al. |
| 2006/0271192 A1 | 11/2006 | Olsen et al. | 2009/0156997 A1 | 6/2009 | Trenhaile |
| 2006/0276793 A1 | 12/2006 | Berry | 2009/0163949 A1 | 6/2009 | Rolnick et al. |
| 2006/0276809 A1 | 12/2006 | Oliveira | 2009/0177233 A1 | 7/2009 | Malek |
| 2006/0280768 A1 | 12/2006 | Hwang et al. | 2009/0192468 A1 | 7/2009 | Stone |
| 2006/0282082 A1 | 12/2006 | Fanton et al. | 2009/0198277 A1 | 8/2009 | Gordon et al. |
| 2006/0282085 A1 | 12/2006 | Stone et al. | 2009/0204146 A1 | 8/2009 | Kaiser et al. |
| 2006/0293709 A1 | 12/2006 | Bojarski et al. | 2009/0228042 A1 | 9/2009 | Koogle, Jr. et al. |
| 2007/0005080 A1 | 1/2007 | Wolniewicz et al. | 2009/0234357 A1 | 9/2009 | Morales et al. |
| 2007/0016305 A1 | 1/2007 | Chudik | 2009/0234358 A1 | 9/2009 | Morales et al. |
| 2007/0021779 A1 | 1/2007 | Garvin et al. | 2009/0240251 A1 | 9/2009 | Gabele |
| 2007/0032800 A1 | 2/2007 | Ortiz et al. | 2009/0248091 A1 | 10/2009 | Teague et al. |
| 2007/0038218 A1 | 2/2007 | Grevious | 2009/0265014 A1 | 10/2009 | May et al. |
| 2007/0043371 A1 | 2/2007 | Teague et al. | 2009/0306711 A1 | 12/2009 | Stone et al. |
| 2007/0055249 A1 | 3/2007 | Jensen et al. | 2009/0312776 A1 | 12/2009 | Kaiser et al. |
| 2007/0055251 A1 | 3/2007 | Huebner et al. | 2009/0318960 A1 | 12/2009 | Burkhart |
| 2007/0055255 A1 | 3/2007 | Siegel | 2009/0318961 A1 | 12/2009 | Stone et al. |
| 2007/0060922 A1 | 3/2007 | Dreyfuss | 2010/0042114 A1 | 2/2010 | Schaffhausen |
| 2007/0067025 A1 | 3/2007 | Schwartz | 2010/0087857 A1 | 4/2010 | Stone et al. |
| 2007/0073307 A1 | 3/2007 | Scribner et al. | 2010/0145384 A1 | 6/2010 | Stone et al. |
| 2007/0078435 A1 | 4/2007 | Stone et al. | 2010/0191342 A1 | 7/2010 | Byrd et al. |
| 2007/0083236 A1 | 4/2007 | Sikora et al. | 2010/0211075 A1 | 8/2010 | Stone |
| 2007/0093847 A1 | 4/2007 | Scribner et al. | 2010/0256677 A1 | 10/2010 | Albertorio et al. |
| 2007/0100350 A1* | 5/2007 | Deffenbaugh et al. ........ 606/104 | 2010/0268273 A1 | 10/2010 | Albertorio et al. |
| 2007/0118217 A1 | 5/2007 | Brulez et al. | 2010/0268275 A1 | 10/2010 | Stone et al. |
| 2007/0123883 A1 | 5/2007 | Ellis et al. | 2010/0270306 A1 | 10/2010 | Shiffer |
| 2007/0142838 A1 | 6/2007 | Jordan | 2010/0292792 A1 | 11/2010 | Stone et al. |
| 2007/0156174 A1 | 7/2007 | Kaiser et al. | 2010/0305698 A1 | 12/2010 | Metzger et al. |
| 2007/0162018 A1 | 7/2007 | Jensen et al. | 2010/0305709 A1 | 12/2010 | Metzger et al. |
| 2007/0185488 A1 | 8/2007 | Pohjonen et al. | 2010/0312341 A1 | 12/2010 | Kaiser et al. |
| 2007/0185532 A1 | 8/2007 | Stone et al. | 2011/0009885 A1 | 1/2011 | Graf et al. |
| 2007/0191849 A1 | 8/2007 | ElAttrache et al. | 2011/0087284 A1 | 4/2011 | Stone et al. |
| 2007/0191853 A1 | 8/2007 | Stone | 2011/0098727 A1 | 4/2011 | Kaiser et al. |
| 2007/0219558 A1 | 9/2007 | Deutsch | 2011/0106153 A1 | 5/2011 | Stone et al. |
| 2007/0239209 A1 | 10/2007 | Fallman | 2011/0160768 A1 | 6/2011 | Stone et al. |
| 2007/0239275 A1 | 10/2007 | Willobee | 2011/0208239 A1 | 8/2011 | Stone et al. |
| 2007/0250163 A1 | 10/2007 | Cassani | 2011/0208240 A1 | 8/2011 | Stone et al. |
| 2007/0260251 A1 | 11/2007 | Weier et al. | 2011/0213416 A1 | 9/2011 | Kaiser |
| 2007/0260279 A1 | 11/2007 | Hotter et al. | 2011/0218625 A1 | 9/2011 | Berelsman et al. |
| 2007/0270856 A1 | 11/2007 | Morales et al. | 2011/0224799 A1 | 9/2011 | Stone |
| 2007/0276387 A1 | 11/2007 | Morales et al. | 2011/0264141 A1 | 10/2011 | Denham et al. |

| | | | |
|---|---|---|---|
| 2011/0270278 A1 | 11/2011 | Overes et al. | |
| 2011/0270306 A1 | 11/2011 | Denham et al. | |
| 2012/0041485 A1 | 2/2012 | Kaiser et al. | |
| 2012/0041486 A1 | 2/2012 | Stone et al. | |
| 2012/0046693 A1 | 2/2012 | Denham et al. | |
| 2012/0053630 A1 | 3/2012 | Denham et al. | |
| 2012/0059417 A1 | 3/2012 | Norton et al. | |
| 2012/0059418 A1 | 3/2012 | Denham et al. | |
| 2012/0197271 A1 | 8/2012 | Astorino et al. | |

FOREIGN PATENT DOCUMENTS

| | | |
|---|---|---|
| AU | 440266 | 10/1967 |
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-2004091412 A1 | 10/2004 |
| WO | WO-2005104992 A1 | 11/2005 |
| WO | WO-2008002550 A2 | 1/2008 |
| WO | WO-2009012021 A1 | 1/2009 |

OTHER PUBLICATIONS

"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.

"JuggerKnot™ Soft Anchor. It's Small. It's strong. And it's all suture . . . " Ordering Information brochure. Biomet Sports Medicine (Jun. 2011) 2 sheets.

"JuggerKnot™ Soft Anchor. Labral Repair," brochure. Biomet Sports Medicine (Apr. 2011) 12 sheets.

"Make your next tendon repair an open-and-shut case. The Teno Fix® Tendon Repair System", Teno Fix® brochure, 2003 (2 pages) Ortheon® Medical.

"Panalok Anchor with PDS II and ETHIBOND Suture", Mitek Products ETHICON, 1997.

"SE Graft Tensioning System Surgical Technique," Linvatec Corporation copyright 2003, 2004.

"Technique for ACL Reconstruction with Acufex Director Drill Guide and Endobutton CL," by Thomas D. Roseberg, copyright 1999 Smith & Nephew.

A. Weiler, et al; Biodegradierbare Interferenzschrauben in der Kreuzbandchirurgie; OP-Journal 14 pp. 278-284; 1998.

Arthrotek, A Biomet Company; Knees; Sure fire Hybrid Meniscal Device.

Arthrotek, A Biomet Company; Sure fire Hybrid Meniscal Device; Launch Date: Fall AANA 2004.

F. Alan Barber, M.D., "Uses and Abuses of Sutures and Anchors," Shoulder Scope, San Diego Shoulder Arthroscopy Library.

F. Alan Barber, M.D., "Using Sutures and Anchors," San Diego Shoulder Arthroscopy Course, 17th Annual Meeting.

Flavia Namie Azato, et al. "Traction endurance biomechanical study of metallic suture anchors at different insertion angles," Acta ortop. bras., vol. 11, No. 1, Sao Paulo, Jan./Mar. 2003.

Hecker AT, et al., "Pull-out strength of suture anchors for rotator cuff and Bankart lesion repairs," Am J Sports Med. 1993.

International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.

International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.

Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.

Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.

Lawhorn, M.D., Keith, MaxFire™ Meniscal Repair Device with Zip Loop™ Technology, Biomet Sports Medicine, Feb. 29, 2008.

Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.

Opus Medical; The AutoCuff System; www.opusmedical.com; 2003.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

ToggleLoc™ Femoral Fixation Device, Arthrotek, Mar. 31, 2006.

Arthrotek, A Biomet Company; Knees; Sure fire Hybrid Meniscal Device. (2005).

"Arthroscopic Meniscal Repair using the Meniscal Cinch™", Surgical Technique brochure. (2008) Arthrex® 6 sheets.

Pioneer® Sternal Cable System (2010).

Rapid Sternal Closure (2006) KLS Martin L.P. http://www.rapidsternalclosure.com/medical/demo.php Web accessed Sep. 8, 2008.

Saxena, Pankaj, MCh, DNB et al., "Use of Double Wires in Sternal Closure, A Useful Technique," Texas Heart® Institute. Journal List>Tex Heart Inst J > v.33(4); (2006).

Zeitani, Jacob, M.D., "A New Sternal Reinforcement Device to Prevent and Treat Sternal Dehiscence," CTSNet.org (Jun. 30, 2008).

Invitation to Pay Additional Fees mailed Jul. 19, 2012, for PCT/US2012/037703 claiming benefit of U.S. Appl. No. 13/109,667, filed May 7, 2011.

US 6,238,418, 05/2001, Schwartz et al. (withdrawn)

* cited by examiner

SOFT TISSUE REPAIR DEVICE AND ASSOCIATED METHODS

CROSS-REFERENCE TO RELATED APPLICATIONS

This application is a divisional of U.S. patent application Ser. No. 12/014,340 filed on Jan. 15, 2008, now U.S. Pat. No. 7,905,904, issued Mar. 15, 2011, which claims the benefit of U.S. Provisional Application No. 60/885,057, filed on Jan. 16, 2007, and of U.S. Provisional Application No. 60/885,062, filed on Jan. 16, 2007, and which is a continuation-in-part of the following applications:

U.S. patent application Ser. No. 11/347,661 filed on Feb. 3, 2006, now U.S. Pat. No. 7,749,250, issued on Jul. 6, 2010;

U.S. patent application Ser. No. 11/935,681 filed on Nov. 6, 2007, now U.S. Pat. No. 7,905,903, issued Mar. 15, 2011;

U.S. patent application Ser. No. 11/869,440 filed on Oct. 9, 2007, now U.S. Pat. No. 7,857,830, issued on Dec. 28, 2010; which is a continuation-in-part of U.S. patent application Ser. No. 11/408,282, filed on Apr. 20, 2006 now abandoned; and U.S. patent application Ser. No. 11/541,506, filed on Sep. 29, 2006, now U.S. Pat. No. 7,601,165, issued on Oct. 13, 2009.

The disclosures of the above applications are incorporated herein by reference.

INTRODUCTION

Tears caused by trauma or disease in fibrous soft tissue, such as cartilage, ligament, or muscle, can be repaired by suturing. Various repair devices have been developed for facilitating suturing and are effective for their intended purposes. Nevertheless, tissue repair devices for facilitating suturing are still desirable.

SUMMARY

The present teachings provide a fibrous tissue repair device that includes first and second tubular anchors having corresponding longitudinal passages. The tissue repair device includes corresponding first and second inserters. Each inserter has a shaft with a distal portion received in the longitudinal passage of the corresponding tubular anchor. A flexible strand couples the first and second anchors.

In some embodiments the anchors are non deformable. In some embodiments, the tissue repair device includes a cannula having a handle and a passage receiving the first and second inserters.

In some embodiments, the fibrous repair device includes a handle, first and second inserters movable relative to the handle, and first and second anchors pre-loaded on corresponding external surfaces of the first and second inserters. The repair device also includes a control mechanism operable to control a deployment sequence of the first and second inserters for deploying the corresponding first and second anchors, such that the second inserter is prevented from deploying the second anchor until the first anchor is deployed by the first inserter.

In some embodiments, the fibrous tissue repair device includes a handle, a first inserter movable relative to the handle, a first anchor pre-loaded on an external surface of the first inserter, and a first slider coupled to the handle for moving the first inserter between deployment and retraction positions. The repair device can also include a second inserter movable relative to the handle, a second anchor pre-loaded on an external surface of the second inserter, and a second slider coupled to the handle for moving the second inserter between deployment and retraction positions. Further, the repair device can include a slider control mechanism coupled to the first and second sliders and operable to control a motion sequence of the first and second inserters, such that the first inserter is constrained to move to a deployment position before the second inserter. The repair device can also include a flexible strand coupling the first and second anchors. The flexible strand can pass through portions of the first and second anchors and form an adjustable knotless loop.

The present teachings also provide a method of repairing fibrous tissue. The method includes preloading a first anchor externally onto a first inserter, passing the first inserter from a first side to a second side of the fibrous tissue at a first location, delivering the first anchor on the second side of the fibrous tissue, and retracting the first inserter away from the tissue.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DESCRIPTION OF VARIOUS ASPECTS

The following description is merely exemplary in nature and is in no way intended to limit the invention, its application, or uses. For example, although the present teachings are illustrated in an application for meniscus repair in knee surgery, the present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone. Additionally, the present teachings can be used for repairing tissue in cardiological, laparoscopic, urological, plastic or other procedures.

Figure 1:
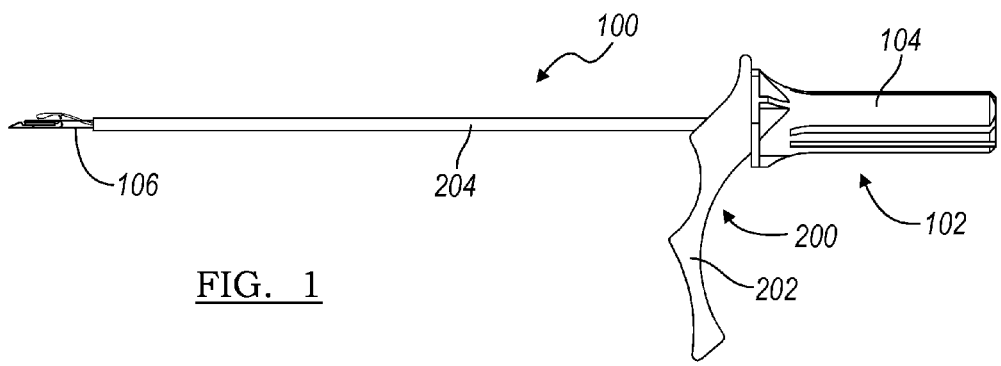
FIG. 1 is side view of a tissue repair device according to the present teachings.
Figure 1A:
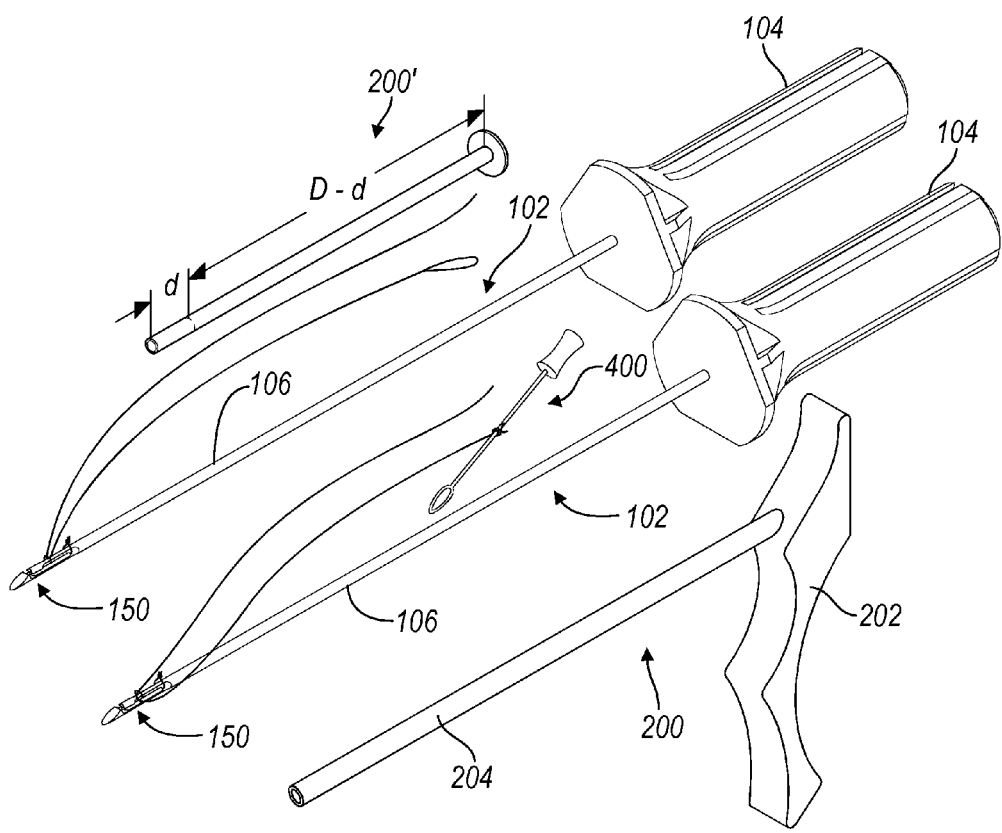
FIG. 1A is a perspective view of a tissue repair kit according to the present teachings.
Figure 2:
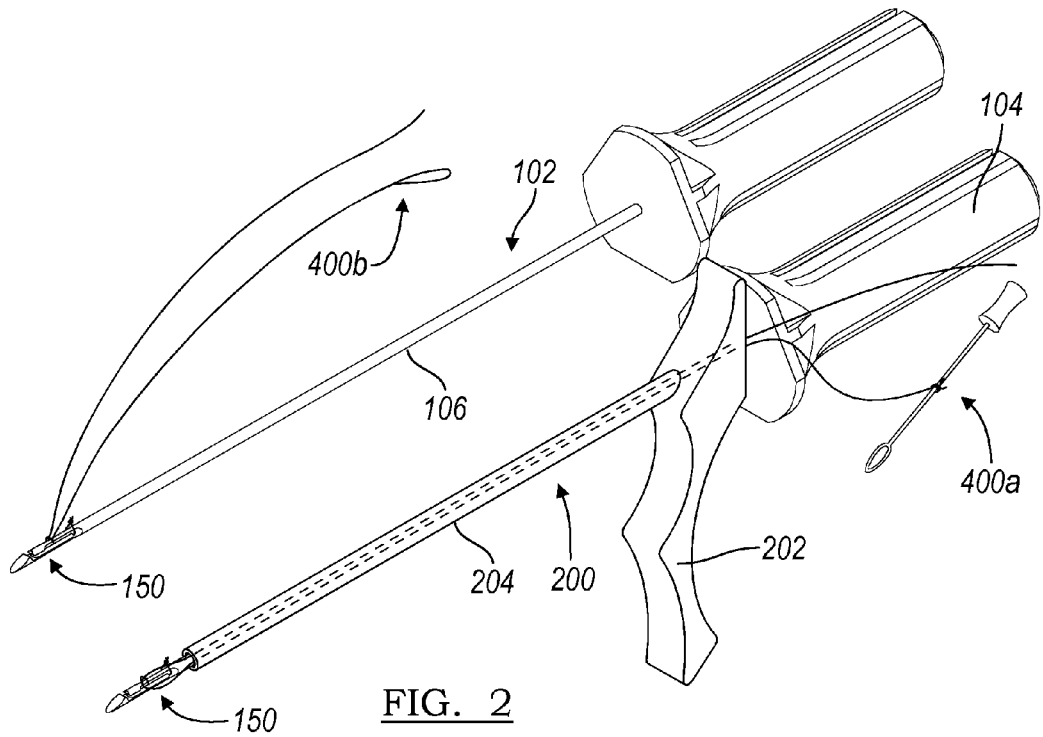
FIG. 2 is a perspective view of a tissue repair device according to the present teachings.
Figure 3:
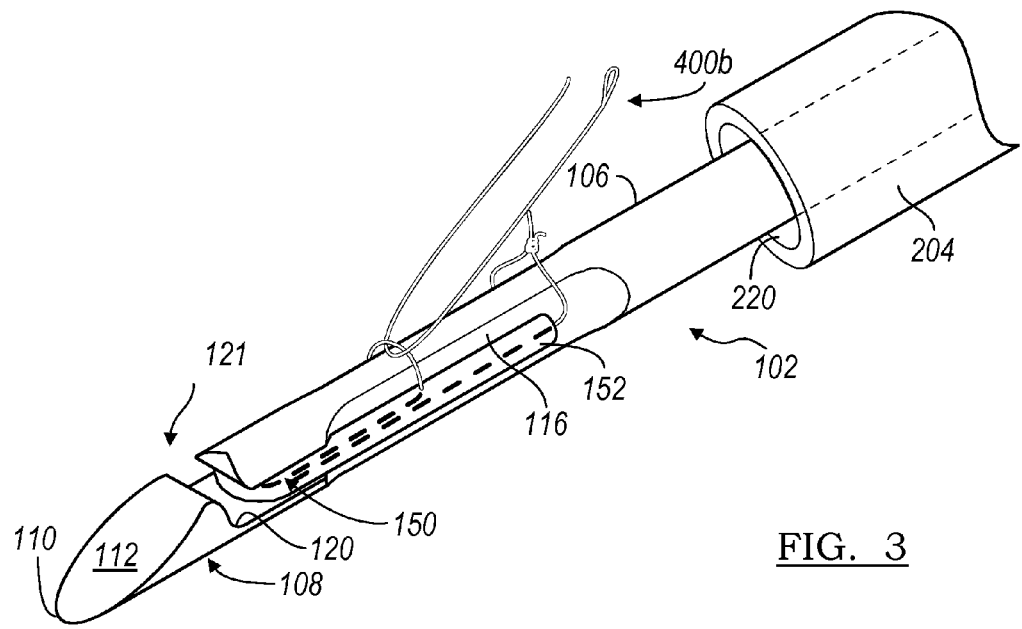
FIG. 3 is an enlarged perspective view of a tissue repair device according to the present teachings.

An exemplary tissue repair device 100 according to the present teachings is illustrated in FIG. 1, and in a kit form in FIG. 1A. The device 100 can include one or more inserters 102 and a cannula 200. The inserters 102 can be single-use, disposable, or sterilizable inserters. Each inserter 102 can be externally pre-loaded on its outer or external surface 121 with a single flexible anchor 150, as described below. The inserter 102 can include a handle 104 and a solid shaft 106 having a solid distal portion 108.

Figure 6:
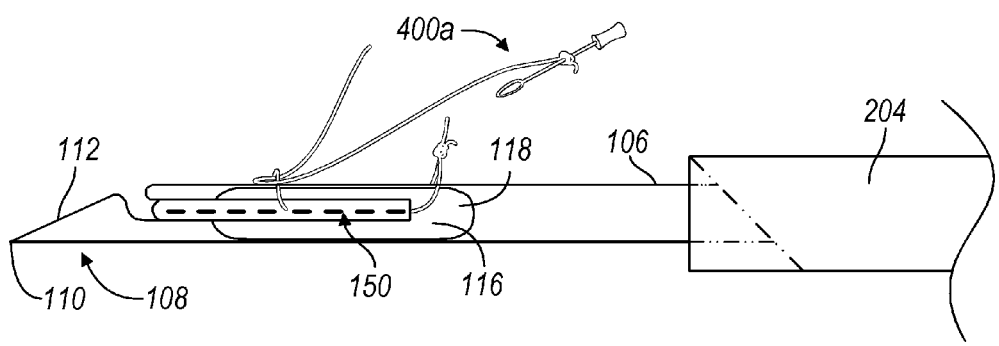
FIG. 6 is an enlarged side view of a tissue repair device according to the present teachings.
Figure 7:
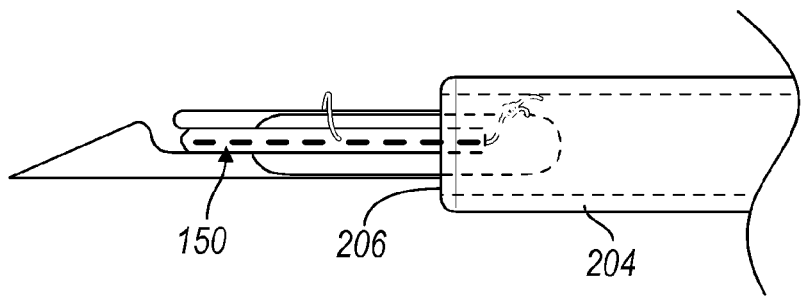
FIG. 7 is an enlarged side view of a tissue repair device according to the present teachings.
Figure 8:
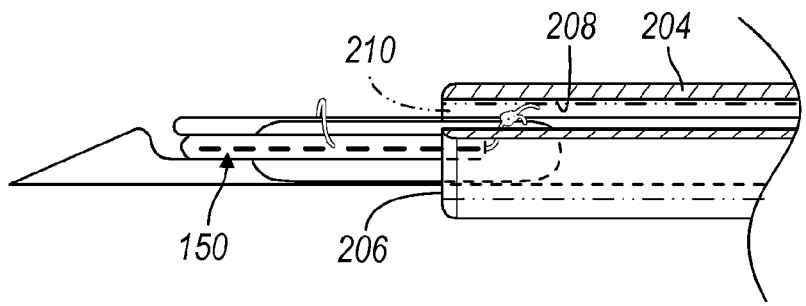
FIG. 8 is an enlarged side view of a tissue repair device according to the present teachings.

Referring to FIGS. 6-8, the distal portion 108 can include a sharp edge 110 defined by an inclined surface 112. The distal portion 108 can also include an external groove or slot 120 which is formed in a direction that is transverse or substantially perpendicular to the shaft 106. The distal portion 108 can also include two opposing substantially planar surfaces 116 defining a buttress 118. It will be appreciated that the outer or external surface 121 of the distal portion 108 incorporates the external groove 120, the planar surfaces 116 and the buttress 118.

The flexible anchor 150 can be an elongated member having first and second ends 152, 154. The flexible anchor 150 can be made of resorbable or non-resorbable materials, including braided suture, sponges and sponge-like materials in solid form, perforated materials, woven/braided from biocompatible materials or fibers, such as, for example, polymer, polyester, polyethylene, cotton, silk, or other natural or synthetic materials, including sponges and sponge-like materials. The flexible anchor 150 can also be an elongated tubular or solid member or a two-dimensional member with or without internal bores. The flexible anchor 150 can have any properties that allow the flexible anchor 150 to change shape. The flexible anchor 150 can be, for example, compliant, flexible, foldable, squashable, squeezable, deformable, limp, flaccid, elastic, low-modulus, soft, spongy, perforated or any other flexible member which can change shape. In some aspects, the flexible anchor 150 can be coated with biological or biocompatible coatings, and it can also be soaked in platelets and other biologics, which can be easily absorbed by the flexible anchor 150 in particular when, for example, the flexible anchor 150 is made from spongy, absorbent material.

Figure 9A:
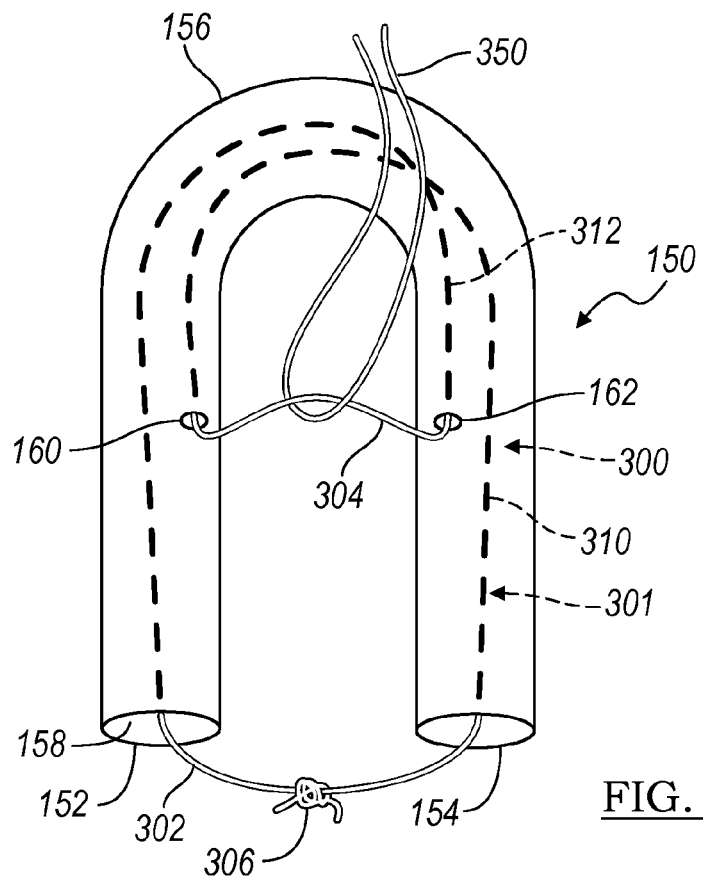
FIGS. 9A-C are perspective views of a flexible anchor shown with flexible strand arrangements according to the present teachings.

It should be understood by the above description that the flexible anchor 150 cannot pierce or otherwise penetrate tissue either with the first and second ends 152, 154 or with any portion thereof. The flexible anchor 150 can be loaded solely on the external surface 121 of the distal portion 108 of the shaft 106 in a folded configuration, such at the first and second ends 152, 154 are facing each other. Accordingly, no portion of the anchor 150 is received even partially in or within the inserter, in contrast to prior art hollow needles and tubes that define an interior tubular surface within which one or more anchors are held substantially in their entirety. More specifically, an intermediate portion 156 of the flexible anchor 150 can be smoothly bent in a substantially U-shape, and draped over the external groove 120, while the first and second ends 152, 154 extend along the flat portions 116 of the shaft 106 of the inserter 102. The flexible anchor 150 can be in the form of an elongate flexible tube defining a bore 158 along its length, as shown in FIG. 9A. The flexible anchor 150 can be formed of suture braided without a core.

Referring to FIGS. 1, 1A, and 6-8, the cannula 200 can include a handle 202 and a tubular or hollow shaft 204. The shaft 204 of the cannula 200 can have a longitudinal bore 220 having an inner diameter sized to receive the shaft 106 of the inserter 102. The shaft 204 of the cannula 200 can have a distal end 206 which can be perpendicular relative to the shaft 204, although it can be also be slanted relative to the shaft 204 as shown in phantom line in FIG. 6. The distal end 206 of the cannula 200 has a rounded, blunt or smooth edge, which is not intended to or capable of piercing or otherwise penetrating tissue, whether the distal end 206 is slanted or perpendicular to the shaft 204.

Referring to FIG. 8, the cannula shaft 204 can include a cut-away slot 208 defining a viewing window 210. The window 210 can be covered with clear plastic, for example in the form of a tubular member 212 received in the bore 220 of the cannula shaft 204.

Figure 4:
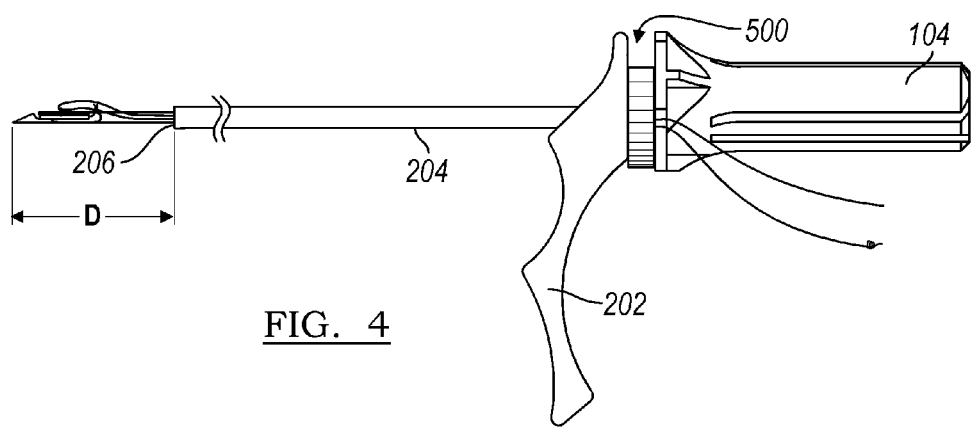
FIG. 4 is a side view of a tissue repair device according to the present teachings shown in a first position.
Figure 5:
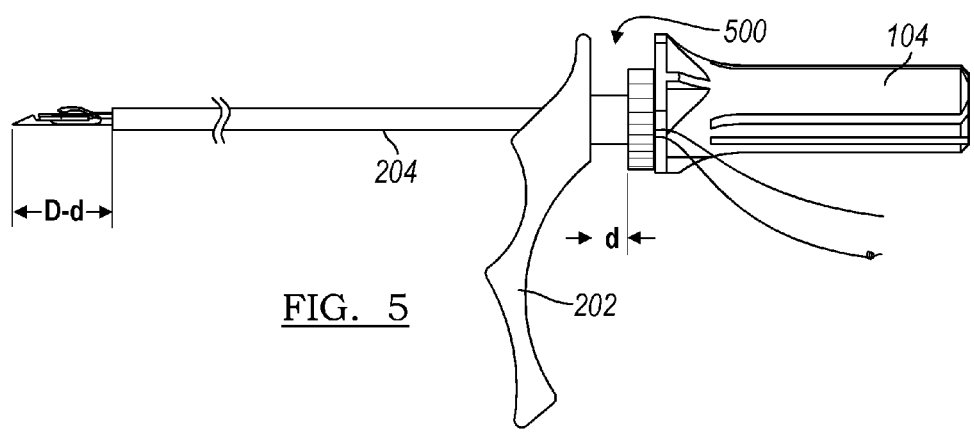
FIG. 5 is a side view of the device of FIG. 4 shown in a second position.

Referring to FIGS. 4 and 5, the soft tissue repair device 100 can be used with a depth limiter 500. The depth limiter 500 can be installed over the shaft 106 of the inserter 102 and between the handle 104 of the inserter 102 and the handle 204 of the cannula 200. The depth limiter can operate as an actuator using, for example, a rack-and-gear mechanism to move the shaft 106 of the inserter 102 relative to the shaft 204 of the cannula 200 between the position shown in FIG. 4, and the position shown in FIG. 5. In the position of FIG. 4, the inserter 102 extends a distance "D" beyond the distal end 206 of the cannula 200. In the position of FIG. 5, the inserter 102 extends a distance "D-d" beyond the distal end 206 of the cannula 200, where "d" is a retraction distance of the depth limiter 500. Alternatively, a separate disposable depth limiter in the form of a plastic tube 200' that can be cut to a desired depth by removing a portion of length "d" can also be used over the shaft 106 of the inserter 102, as shown in FIG. 1A. The cannula 200, on the other hand, can be reusable.

Referring to FIGS. 1A and 9A-9C, the flexible anchor 150 can be assembled bent in a U-shape form on the inserter 102 with a continuous strand loop 300 attached thereon. The strand loop 300 can be formed by a single segment of flexible strand 301 passing through the bore 158 of the anchor 150, such that the strand loop 300 includes a first external segment or portion 302 outside the bore 158 and between the ends 152, 154, and a second external segment portion 304 located outside the bore 158 and exiting the bore 158 from exit positions or openings 160, 162 on opposite sides of the bent U-shape of the flexible anchor 150. The flexible strand 301 can be made of braided filaments or fibers of biocompatible material, including natural and synthetic fibers, such as cotton, silk, polymer, polyester, polyethylene, thin wire, suture, and other materials.

Figure 9B:
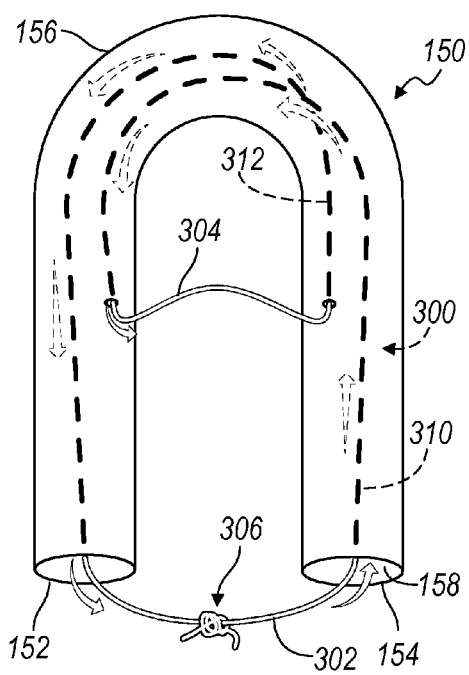
Figure 9C:
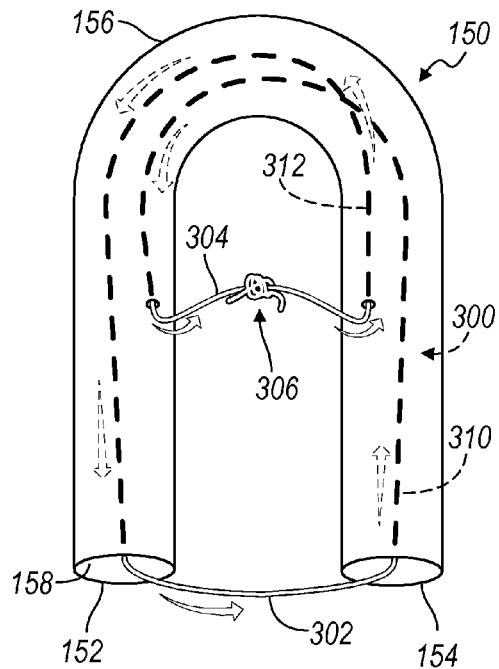

The strand loop 300 can be formed by tying the ends of the segment with a knot 306 which can be positioned on either the first external portion 302 or the second external portion 304, as shown in FIGS. 9B and 9C respectively. It will be appreciated that the loop 300 can define first and second secondary loops or sub-loops 310, 312. The first sub-loop 310 can include the first external portion 302, and the second sub-loop can include the second external portion 304. The first and second sub-loops 310, 312 can intersect each other, and each sub-loop 310, 312 can pass through the bent portion of the bore 158 corresponding to the intermediate portion 156 of the flexible anchor 150.

Figure 10:
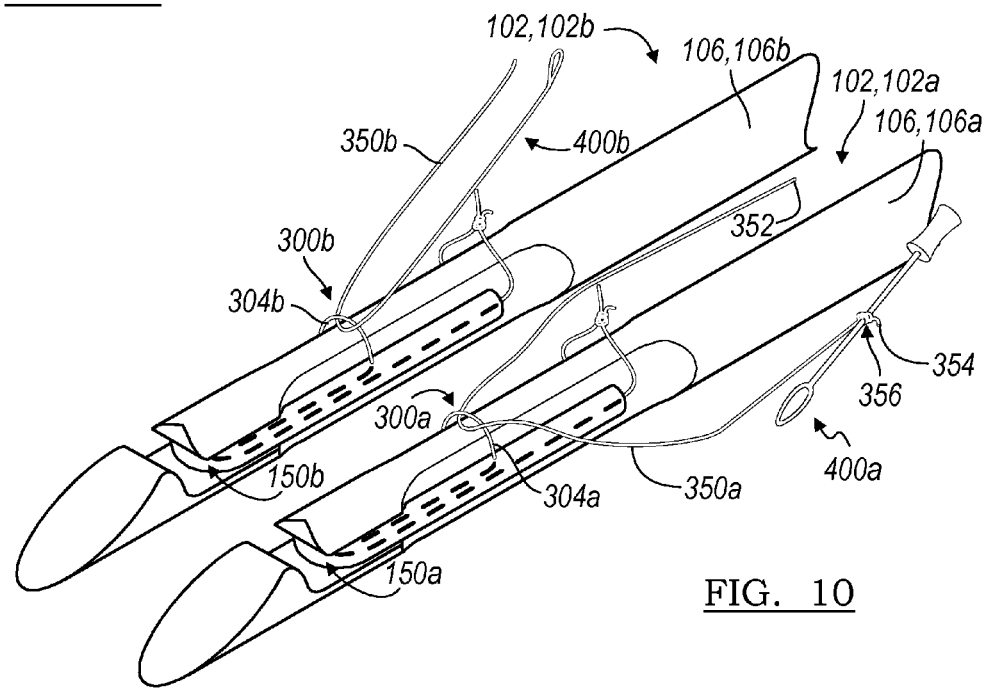
FIG. 10 is a perspective view of two pre-loaded inserters according to the present teachings.
Figure 11:
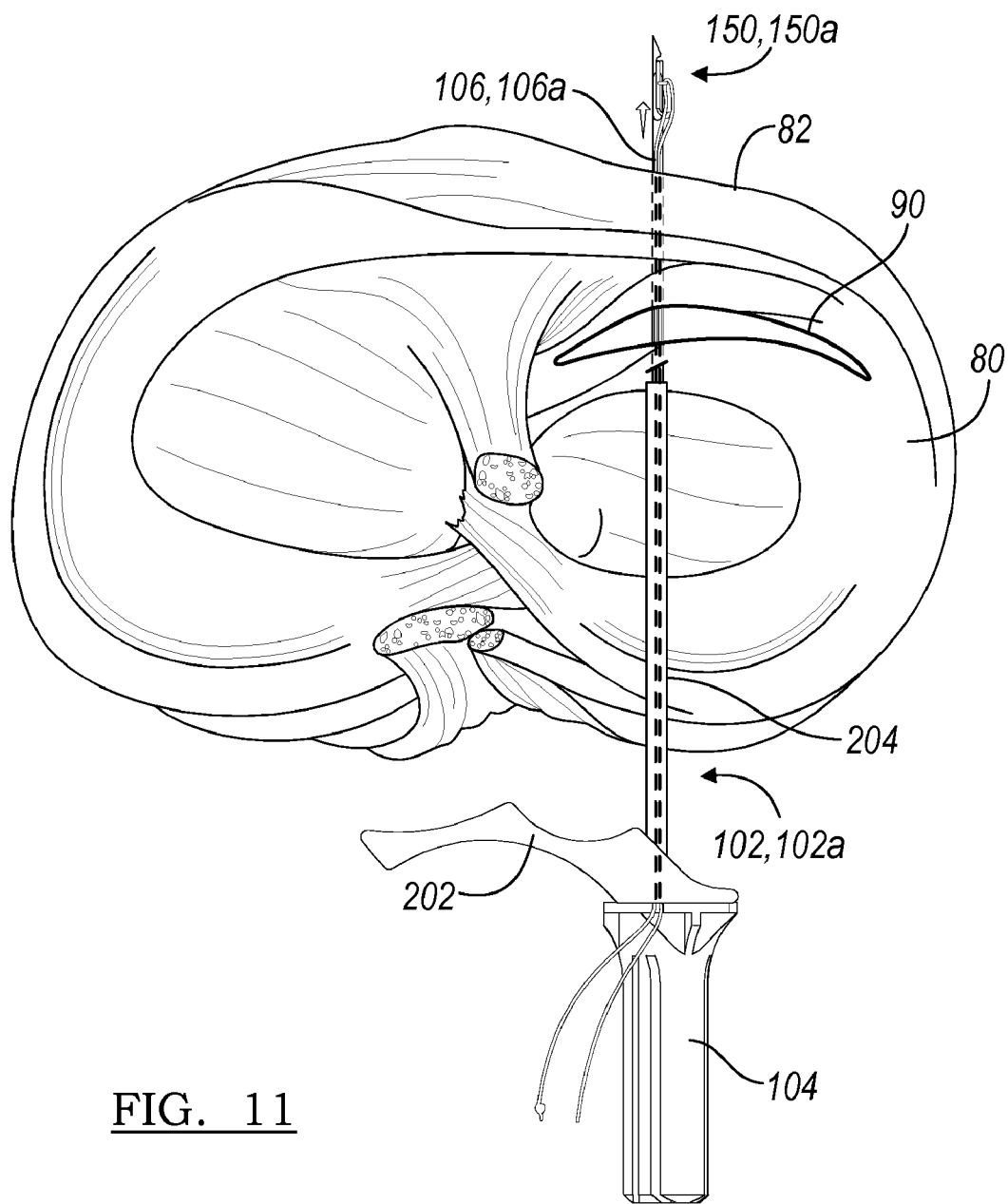
FIG. 11 is an environmental view illustrating inserting a first anchor through soft tissue according to the present teachings.

Referring to FIGS. 10-15, the soft tissue repair device 100 can be used to repair a soft tissue defect 90, such as, for example, a tear, or other weakness in fibrous soft tissue 80, such as in meniscal tissue, cartilage, muscle or other fibrous tissue under the skin. After an outer incision is made through the skin to access the soft tissue 80, the cannula 200 can be positioned through the incision without cutting or piercing any tissue and placed adjacent the soft tissue 80, such as fibrous meniscal tissue, and operate as an access portal for the inserter 102, as shown in FIG. 11. In the following exemplary procedure, the kit of FIG. 1A that includes first and second inserters 102 can be used with the cannula 200 to repair the soft tissue 80. The first and second inserters 102 and their respective features, although identical, will be distinguished for descriptive clarity by appending the letters "a" and "b", e.g. inserters 102a, 102b, shafts 106a, 106b, etc., when desirable for further clarity. Similarly, the associated anchors 150 and their features, as well as other devices used in the procedure will also be distinguished, by appending the letters "a" and "b", when desirable for further descriptive clarity.

Referring to FIG. 10, the first inserter 102a can be assembled with the first anchor 150a externally coupled thereon, as shown. A first flexible strand 350a having a first "free" end 352 and a second end 354 can be coupled on a first threader 400a with a slip knot 356. The first strand 350a can pass through the first strand loop 300a at the second external portion 304a. The second inserter 102b can be assembled with the second anchor 150b externally coupled thereon, as shown. A second strand 350b coupled to a second threader 400b can pass through the second strand loop 300b at the second external portion 304b of the second anchor 150b. Accordingly, the first and second inserters 102a, 102b can be independently pre-assembled, such that the first and second anchors 150a, 150b are only connectable to each other intraoperatively.

Figure 12:
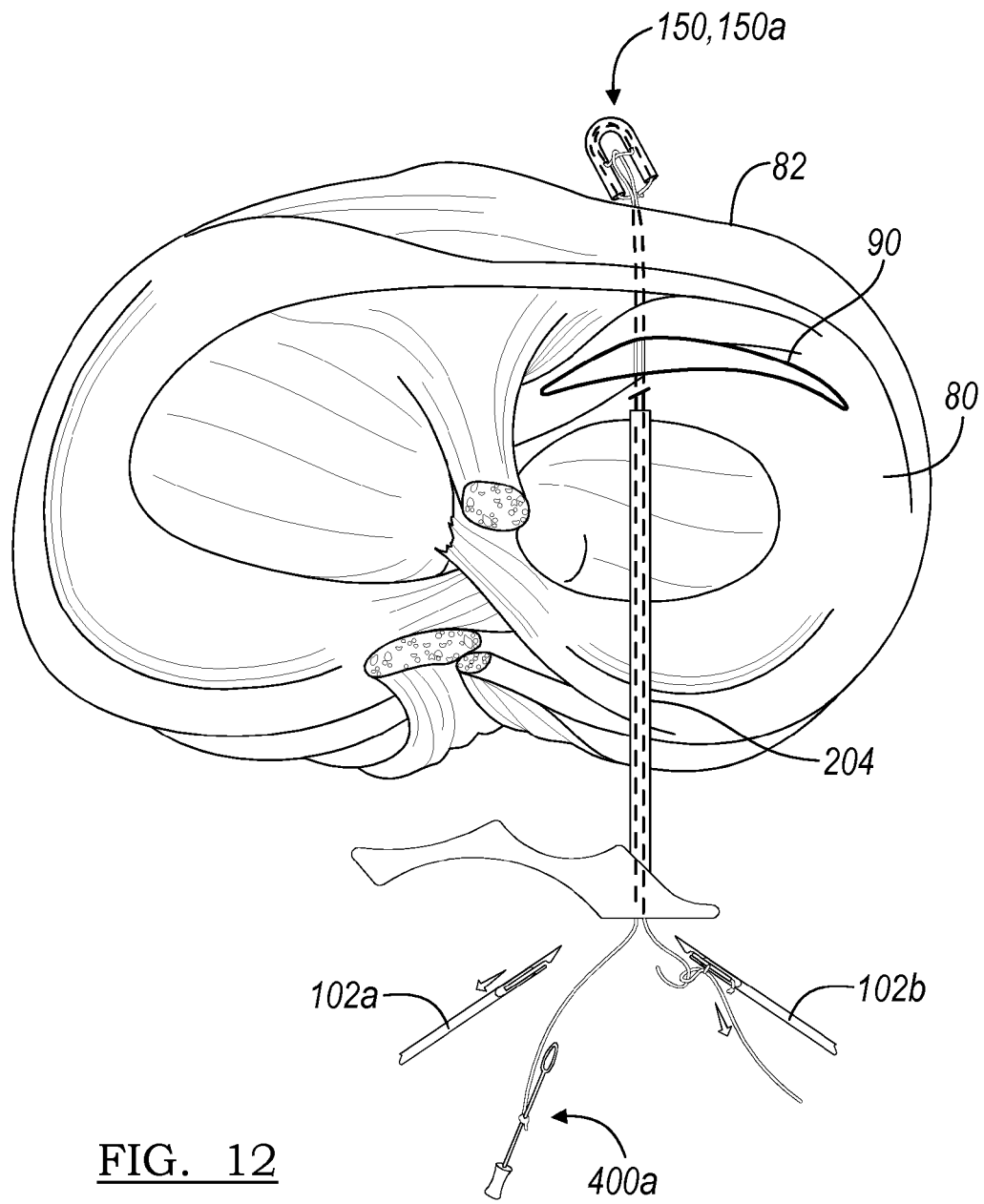
FIG. 12 is an environmental view illustrating delivering a first anchor on an outer surface of soft tissue according to the present teachings.

Referring to FIGS. 11-14, in an exemplary meniscal repair of a knee joint, the cannula 200 can be passed through the incision into the knee joint without piercing any fibrous tissue, except the tissue of the knee joint capsule, and positioned adjacent the meniscus. The first inserter 102a can be passed through the cannula 200 and into the soft tissue 80 or meniscus from a first side of the defect 90 until the shaft 106a of the first inserter 102a can exit a second side 82 of the soft tissue 80, such as an outer surface or back side of the meniscus of the knee joint or other outer surface of a fibrous tissue, for example. The shaft 106a of the first inserter 102a can be sufficiently pushed through the second side 82 of the soft tissue 80 such that upon retraction of the first shaft 106a, the first anchor 150a can be pulled off the first shaft 106a by the spontaneously closing tissue and remain on the second side 82 of the soft tissue 80 at a first location, as shown in FIG. 12. The first inserter 102a can then be removed and discarded.

Figure 9D:
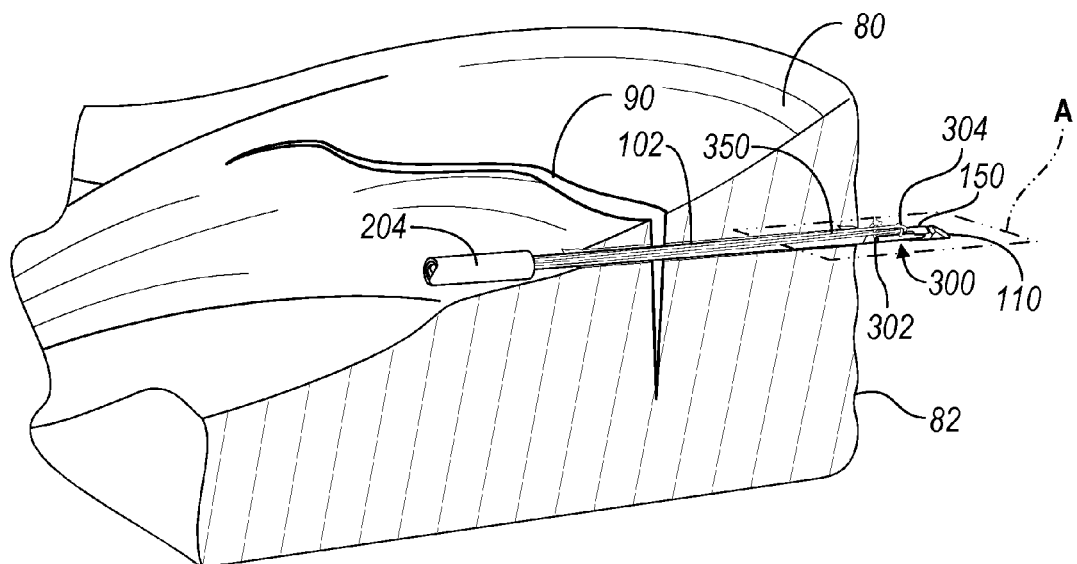
FIG. 9D is a perspective view illustrating a first configuration and a first orientation of an anchor relative to soft tissue according to the present teachings.
Figure 9E:
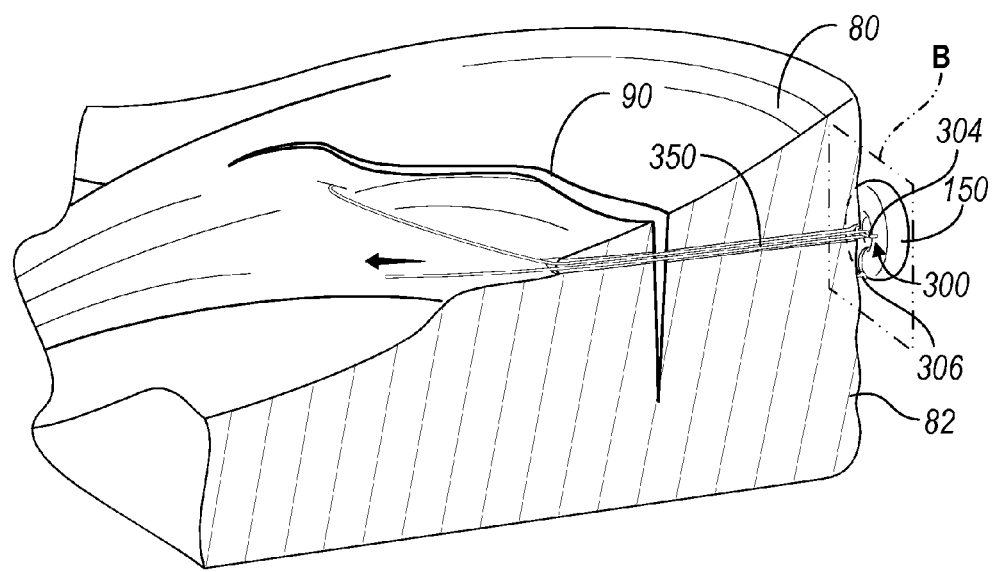
FIG. 9E is a perspective view illustrating a second configuration and a second orientation of the anchor of FIG. 9E relative to soft tissue according to the present teachings.

It will be appreciated that the manner and structure of the pre-assembled inserter 102 and anchor 150 allows the anchor 150 to pass through a narrow opening or slit formed in the tissue 80 by the edge 110 of the inserter 102 in a first low-profile folded configuration defining a plane "A", as shown in FIG. 9D, and deposited in that configuration outside the tissue 80. It will be appreciated that the flexible anchor 150 is deployed in its U-shape configuration with the first and second ends 152, 154 being delivered substantially simultaneously. Further, it will be understood that tightening the first strand loop 300 by pulling on the second external portion 304 can cause the anchor 150 to deform to a second configuration having a substantially flat round-like or knurled shape. Further pulling on the second external portion 304 can rotate the first anchor 150a from a first orientation defined by plane A and substantially perpendicular to the outer surface 82 to a second orientation such that the deformed anchor 150 can define a plane "B" substantially parallel to and lying on the outer surface 82 of the soft tissue 80 in a substantially flat shape, as shown in FIG. 9E.

Figure 13:
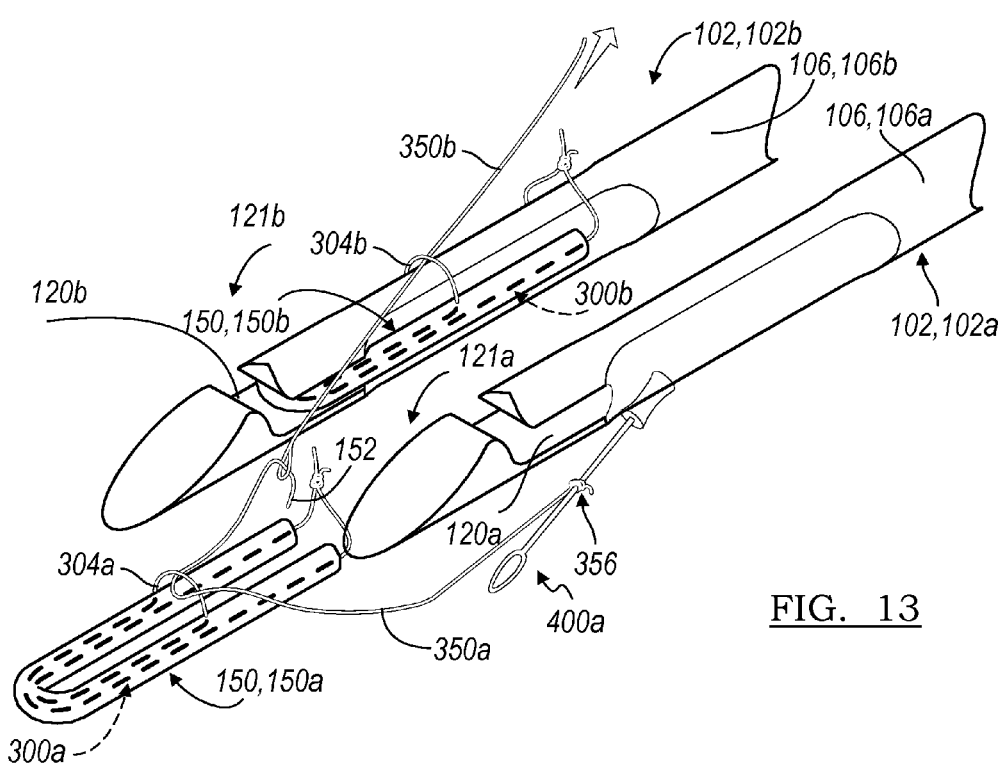
FIG. 13 is a perspective view illustrating connecting a flexible strand between first and second anchors according to the present teachings.
Figure 14:
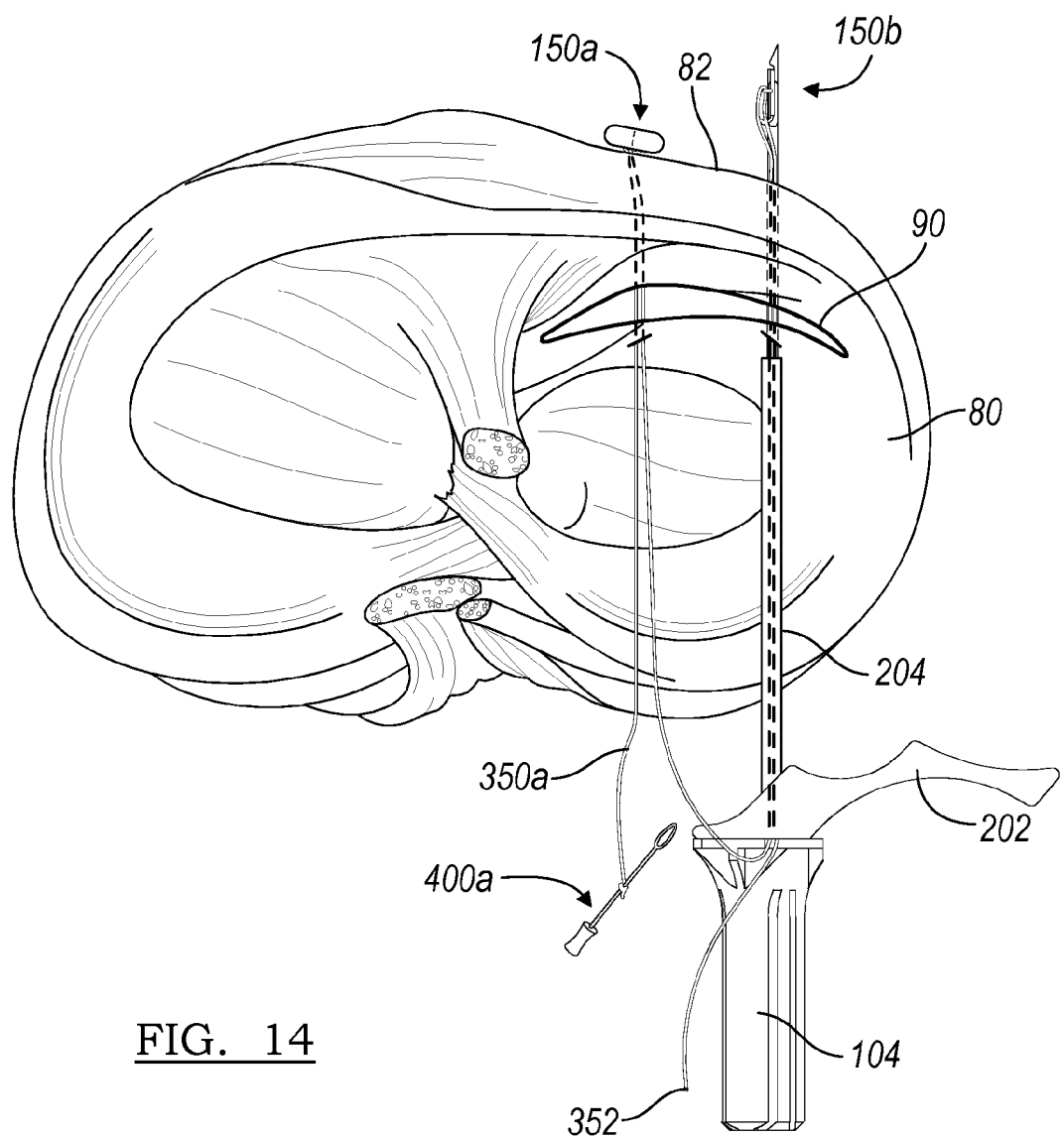
FIG. 14 is an environmental view illustrating delivering a second anchor on an outer surface of soft tissue according to the present teachings.

Referring to FIGS. 13 and 14, the first strand 350a can be captured by the second threader 400 and passed through the second external portion 304b of the second strand loop 300b of the second anchor 150b, which is pre-loaded on the second inserter 102b, as shown in FIG. 13. The second inserter 102b can be inserted through the cannula 200 which is positioned adjacent but without piercing the fibrous tissue as described above, and the second anchor 150b can be delivered to the second side 82 of the soft tissue 80 at a second location, as shown in FIG. 14. The second inserter 102b can then be removed and discarded.

Figure 15:
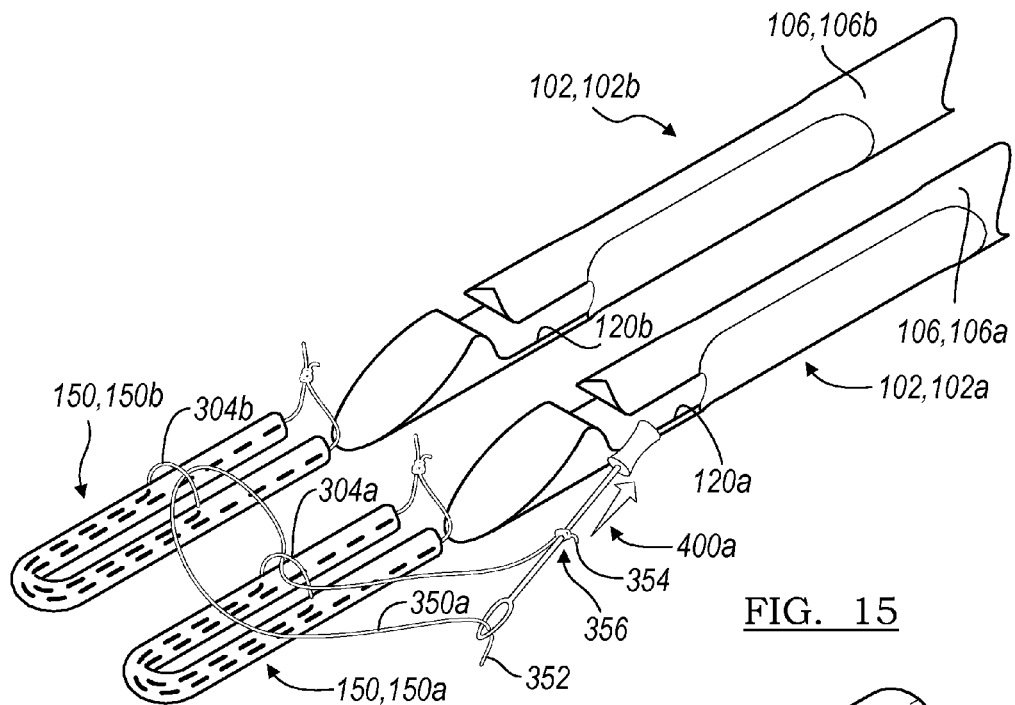
FIG. 15 is a perspective view illustrating passing a free end of flexible strand connecting first and second anchors through a slip knot according to the present teachings.
Figure 16:
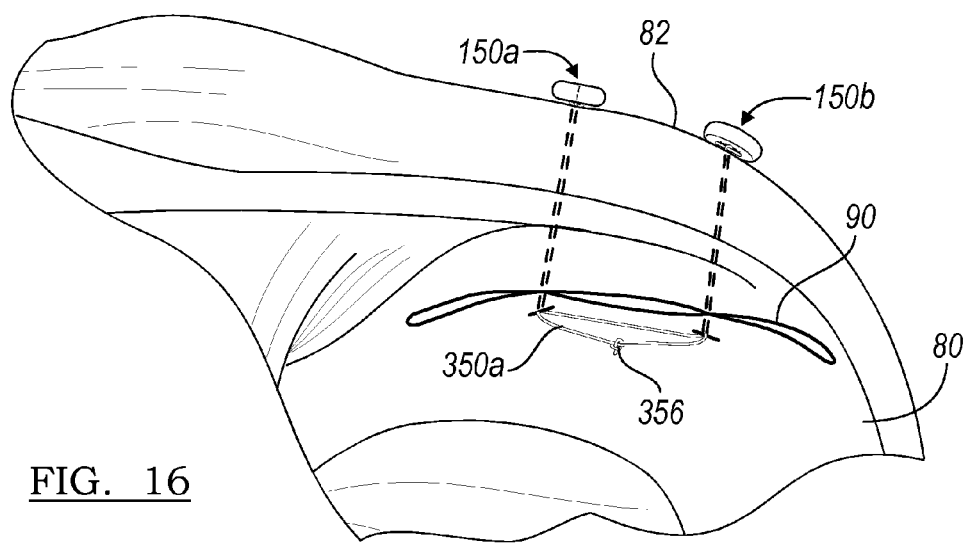
FIG. 16 is an environmental view illustrating a soft tissue defect repair with two anchors according to the present teachings.

Referring to FIG. 15, the first strand 350a can be captured by the first threader 400a, and the free end 352 can be passed through the slip knot 356. The free end 352 of the first strand 350a can be tensioned, thereby deforming each of the anchors 150a, 150b to a substantially flat round-like or knurled shape that can lie substantially flat on the second side 82 of the soft tissue, and compressing the defect 90. Any excess portion of the first strand 350a can be cut off, as shown in FIG. 16. It will be appreciated that more than two anchors 150 can be deployed using a corresponding number of inserters 102. The additional anchors 150 can be connected with the first strand 350a after the second anchor 150b is deployed in the manner described above. Alternatively, additional anchors 150 can be connected independently of the first and second anchors 150a, 150b, either in pairs or singly.

Figure 15A:
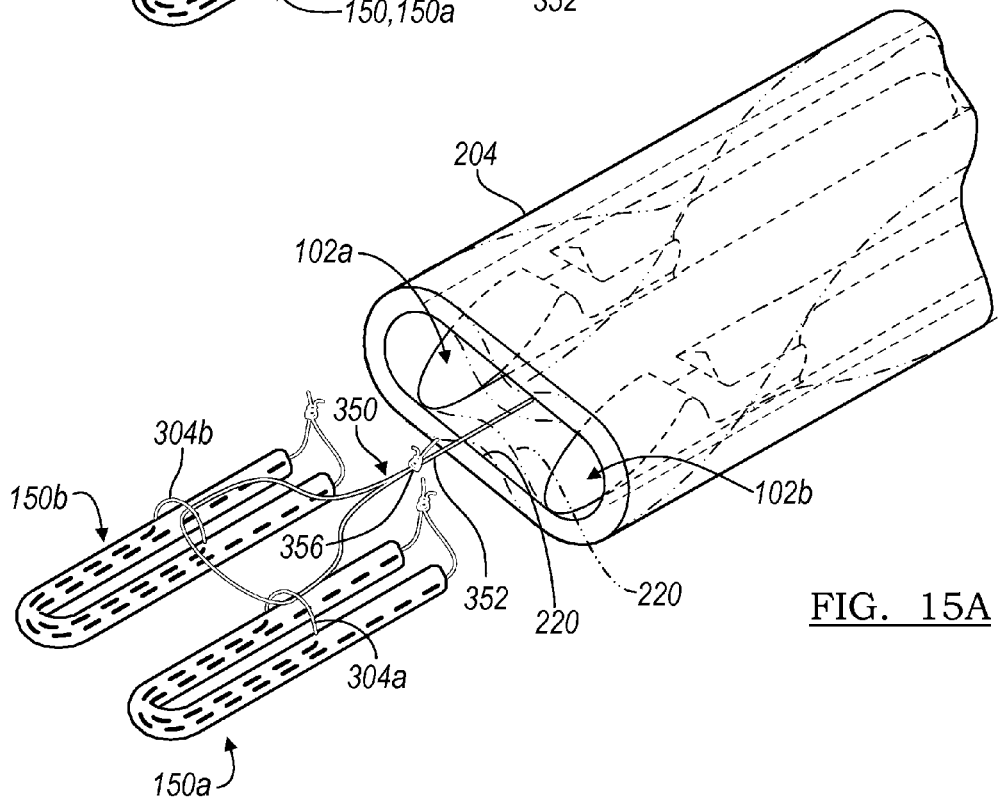
FIG. 15A is a perspective view illustrating first and second anchors connected by a flexible strand according to the present teachings.
Figure 15B:
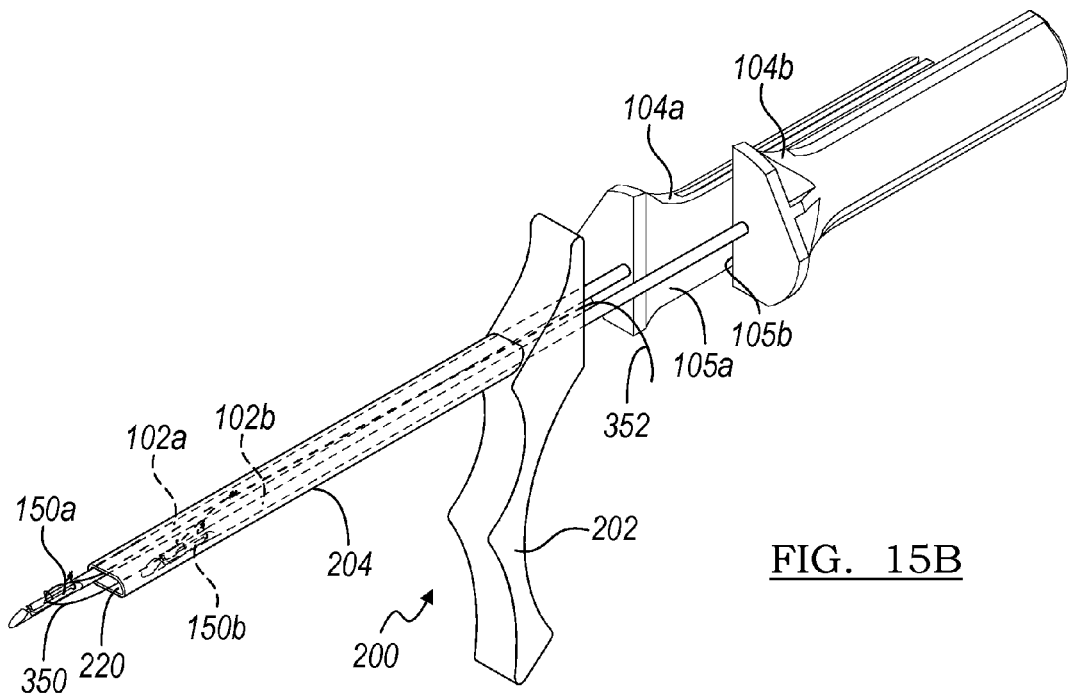
FIG. 15B is a perspective view of a soft tissue repair device according to the present teachings.

Referring to FIGS. 15A and 15B, the flexible strand 350 can be pre-loaded on the first and second anchors 150, 150b, with the free end 352 passing through the slip knot 356, as shown. The first and second anchors 150a, 150b can be deployed as described above using the first and second inserters 102a, 102b with the interconnected anchors 150a, 150b assembled thereon. The bore 220 of the hollow shaft 204 of the cannula 200 can have an elongated shape, or an eight-like shape shown in phantom lines in FIG. 15A, for receiving both the first and second inserters 102a, 102b sequentially or simultaneously. The handles 104a, 104b of the first and second inserters 102a, 102b can have corresponding flat surfaces 105a, 105b, facing one another and slidable relative to one another, such that each of the first and second inserters 102a, 102b can be independently inserted into or retracted from the cannula bore 220 without interference or obstruction from the other.

Alternative loop arrangements for coupling and deforming flexible anchors 150a, 150b are discussed below in reference with FIGS. 33-38.

Figure 18:
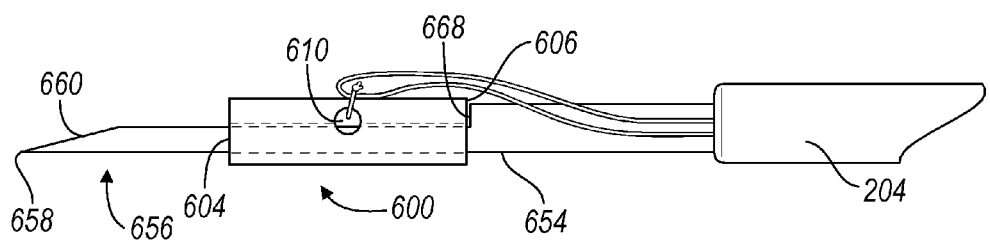
FIG. 18 is an enlarged side view of the device of FIG. 17.
Figure 19:
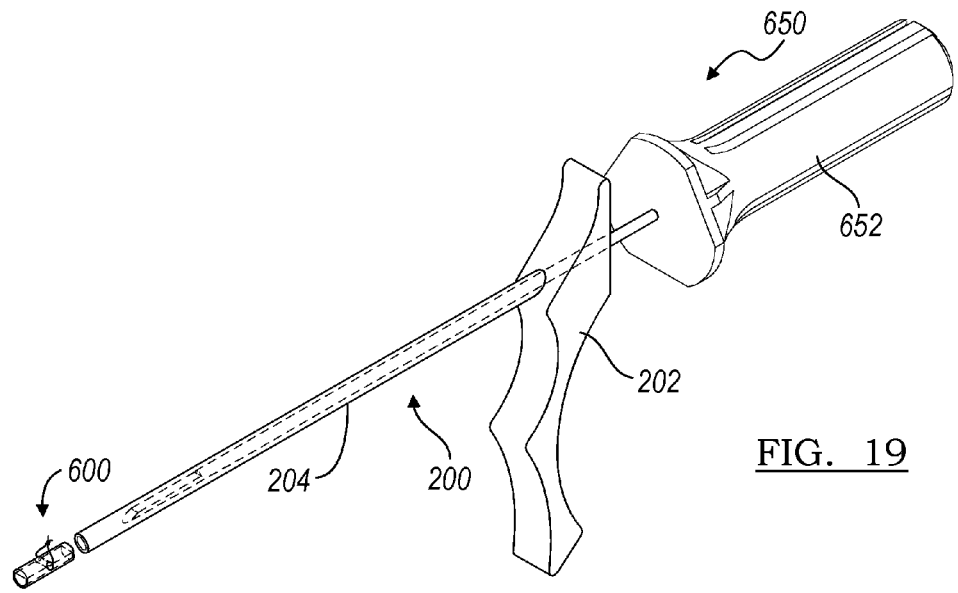
FIG. 19 is an exploded view of FIG. 17.
Figure 20:
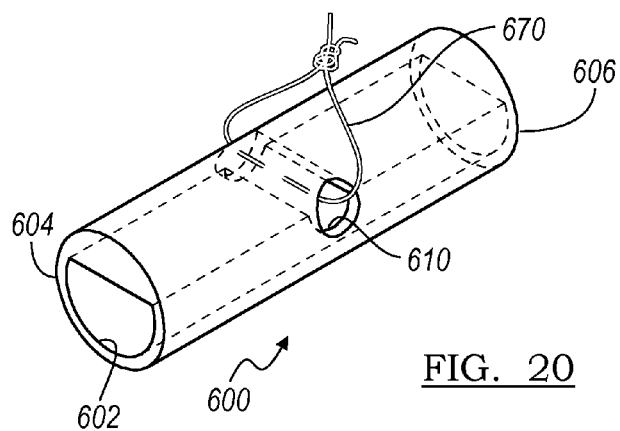
FIG. 20 is a perspective view of an anchor according to the present teachings.

Referring to FIGS. 17-26, a similar procedure can be used to repair a defect 90 in soft tissue 80 using a non-deformable or substantially rigid anchor 600. The anchor 600 can be made of any biocompatible material, such as, for example, titanium or other non-resorbable or resorbable material, including polymeric materials and Lactosorb® commercially available from Biomet, Inc., Warsaw, Ind. Referring to FIG. 20, the anchor 600 can be tubular defining a longitudinal bore 602 that extends between first and second ends 604, 606 of the anchor 600. The longitudinal bore 602 can be substantially D-shaped. The ends 604, 606 of the anchor 600 have blunt rounded edges substantially perpendicular to the anchor 600, such that the ends 604, 606 are not capable and not intended for piercing or penetrating tissue. The anchor 600 can further define a transverse bore 610 oriented at an angle to the longitudinal bore 602, such as, for example, 90-degrees or other suitable angle relative to the longitudinal bore 602. A flexible strand loop 620 can be passed through the transverse bore 610.

Alternative non-deformable anchors and loop arrangements are discussed below in reference with FIGS. 39A-41.

Figure 17:
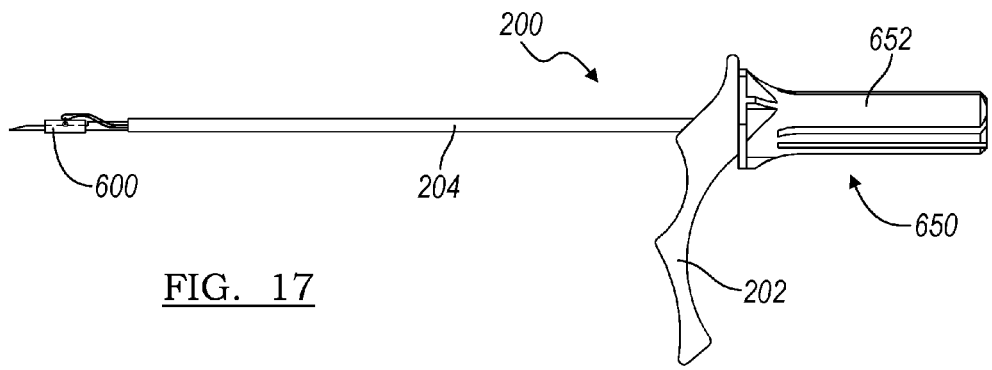
FIG. 17 is side view of a tissue repair device according to the present teachings.

Referring to FIG. 17-19, the anchor 600 can be inserted in tissue using an inserter 650 similar to the inserter 102 shown in FIG. 1A, but configured to be coupled with the anchor 600. The inserter 650 can be used with the cannula 200, as described above. The inserter 650 can include a handle 652, and a solid shaft 654 having a solid distal portion 656. The distal portion 656 can terminate at a sharp edge 658 defined by a slanted surface 660. The distal portion 656 can include a buttress or stop 668 on which the second end 606 of the anchor 600 can abut, as shown in FIG. 18. The distal portion 656 that extends between the slanted surface 660 and the buttress 668 can have a D-shaped cross-section configured to be received in the D-shaped longitudinal bore 602 of the anchor 600 in a keyed manner that does not permit relative rotation between the anchor 600 and the shaft 654.

The inserter 650 and anchor 600 can be used for fibrous tissue repair as described above in reference to FIGS. 10-16. In one exemplary procedure, illustrated in FIGS. 21-23, first and second disposable inserters 650a and 650b independently pre-assembled with first and second anchors 600a, 600b, respectively, can be used. Each anchor 600a, 600b can include a corresponding strand loop 670a, 670b passing through each transverse bore 610a, 610b. A first flexible strand 680 having a first or free end 682 and a second end 684 can be passed through the first strand loop 670a and coupled with a slip knot 686 to a first threader 400a. Similarly, a second flexible strand 680b coupled to a second threader 400b can pass through the second strand loop 670b.

Figure 27:
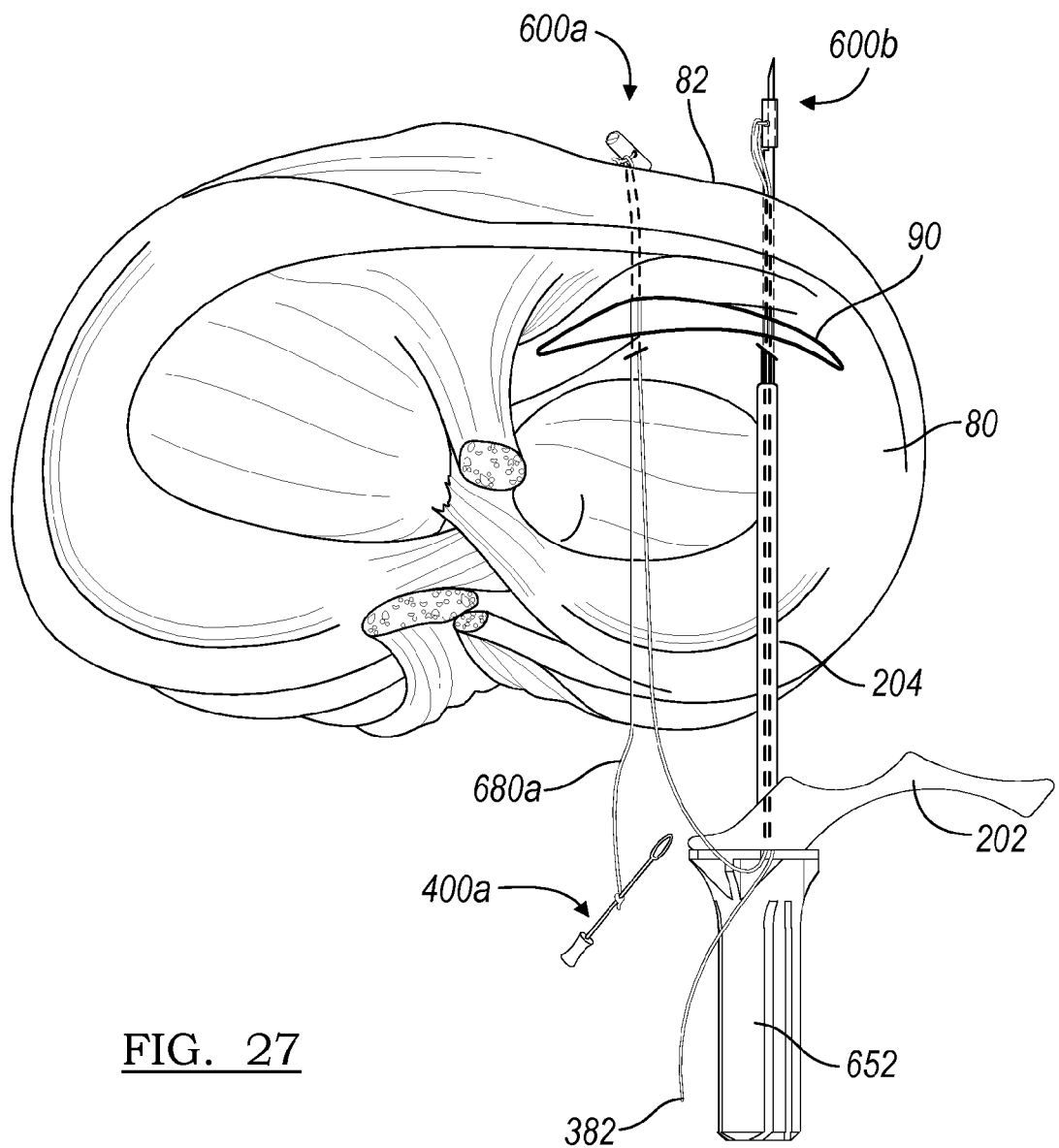
FIG. 27 is an environmental view illustrating delivering a second anchor on an outer surface of soft tissue according to the present teachings.

The first inserter 650a can be passed through the cannula 200 into the soft tissue 80 from a first side of the defect 90 until the shaft 654a of the first inserter 650a can exit the second side 82 of the fibrous soft tissue 80, such that upon retraction of the first shaft 654a, the first anchor 650a can be pulled off the first shaft 654a by the closing tissue and remain on the second side 82 of the soft tissue 80 at a first location, as shown in FIG. 27. The first inserter 650a can then be removed and discarded.

Figure 22:
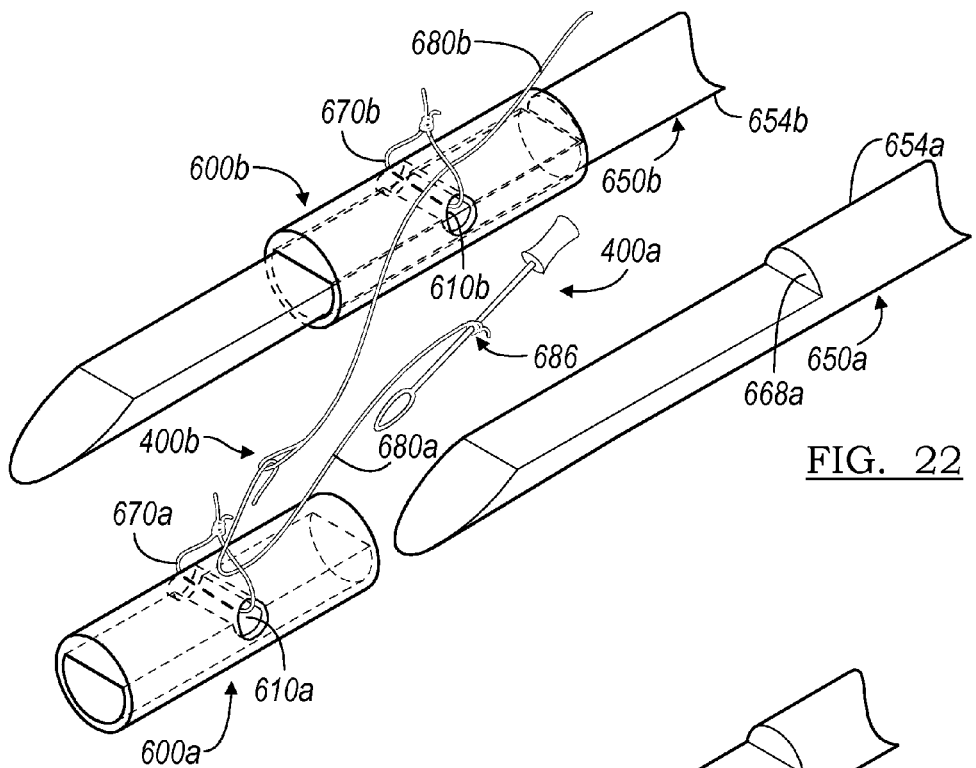
FIG. 22 is a perspective view illustrating connecting a flexible strand between first and second anchors according to the present teachings.

The first strand 680a can be captured intra-operatively by the second threader 400b and passed through the second strand loop 670b of the second anchor 600b which is pre-loaded on the second inserter 650b, as shown in FIG. 22. The second inserter 650b can be inserted through the cannula 200 and the second anchor 600b can be delivered to the second side 82 of the soft tissue 80 at a second location, as shown in FIG. 27. The second inserter 650b can be removed and discarded.

Figure 23:
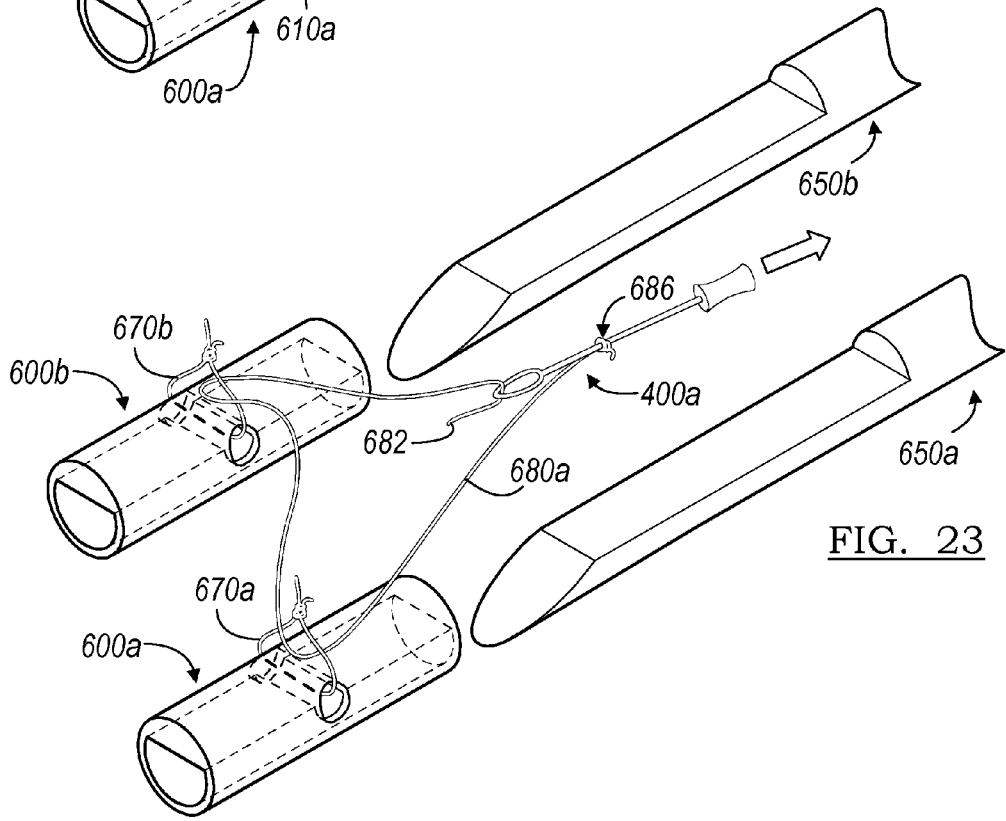
FIG. 23 is a perspective view illustrating passing a free end of flexible strand connecting first and second anchors through a slip knot according to the present teachings.

Referring to FIG. 23, the first strand 680a can be captured by the first threader 400a and the free end 682 can be passed through the slip knot 686. The free end 682 of the first strand 680a can be tensioned, thereby rotating the anchors 600a, 600b such that each anchor 60a, 600b is positioned with its longitudinal axis parallel to the surface of the second side 82 of the soft tissue 80. Tensioning the first strand 680a further can compress the defect 90. Any excess portion of the first strand 680a can be cut off, as shown in FIG. 27.

Figure 21:
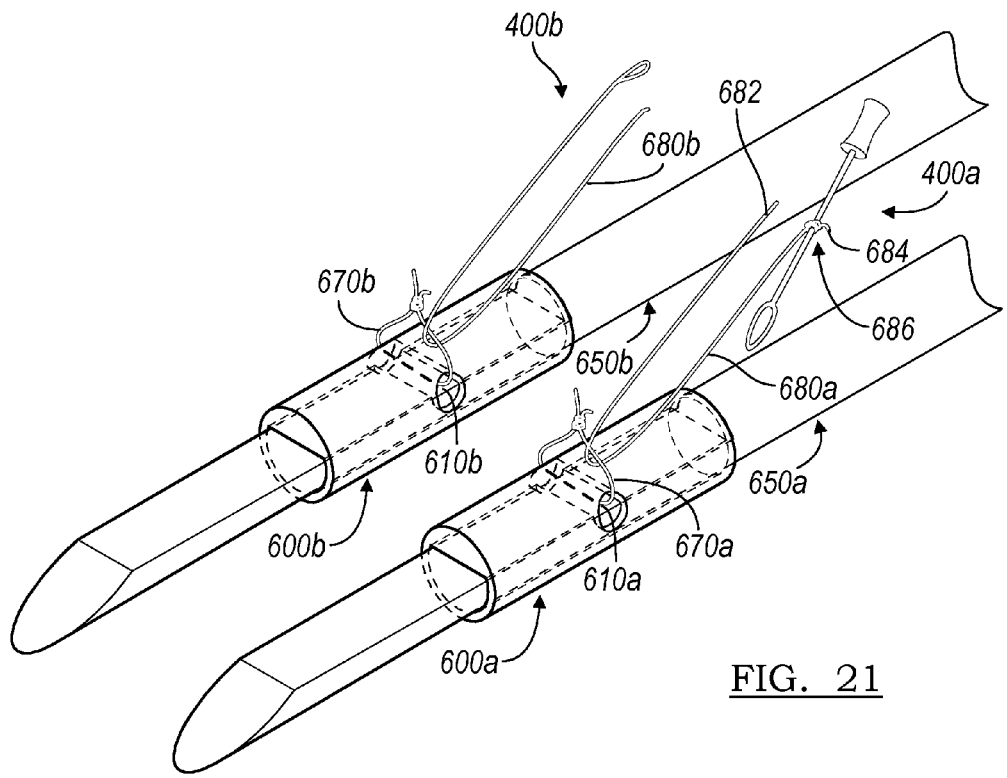
FIG. 21 is a perspective view of two pre-loaded inserters according to the present teachings.
Figure 24:
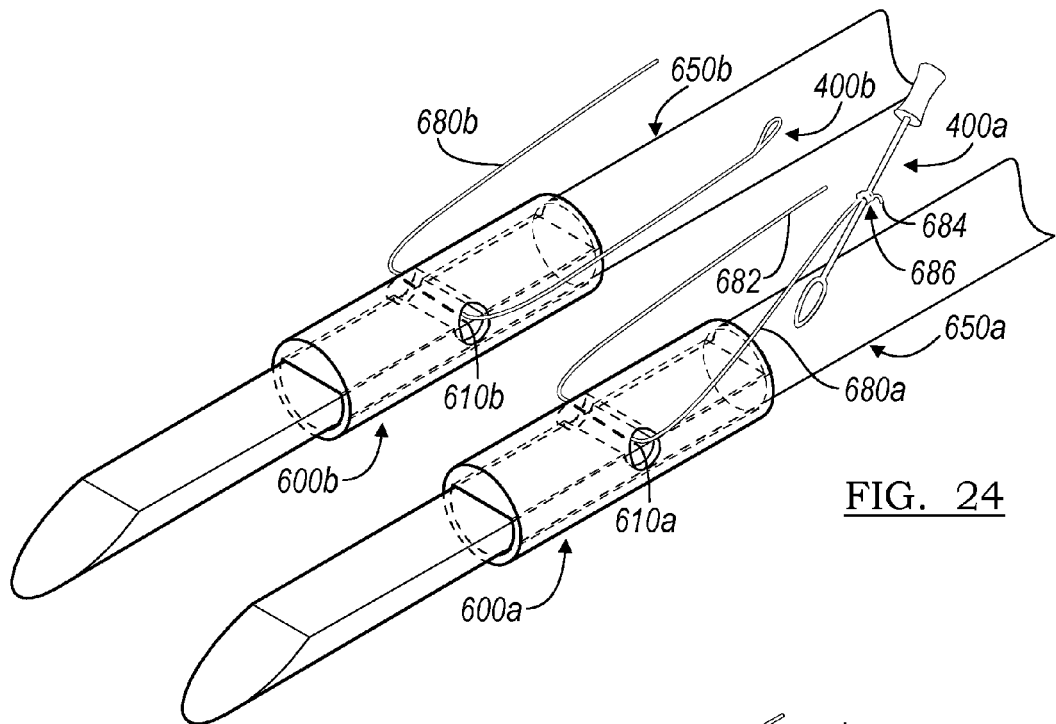
FIG. 24 is a perspective view of two pre-loaded inserters according to the present teachings.
Figure 25:
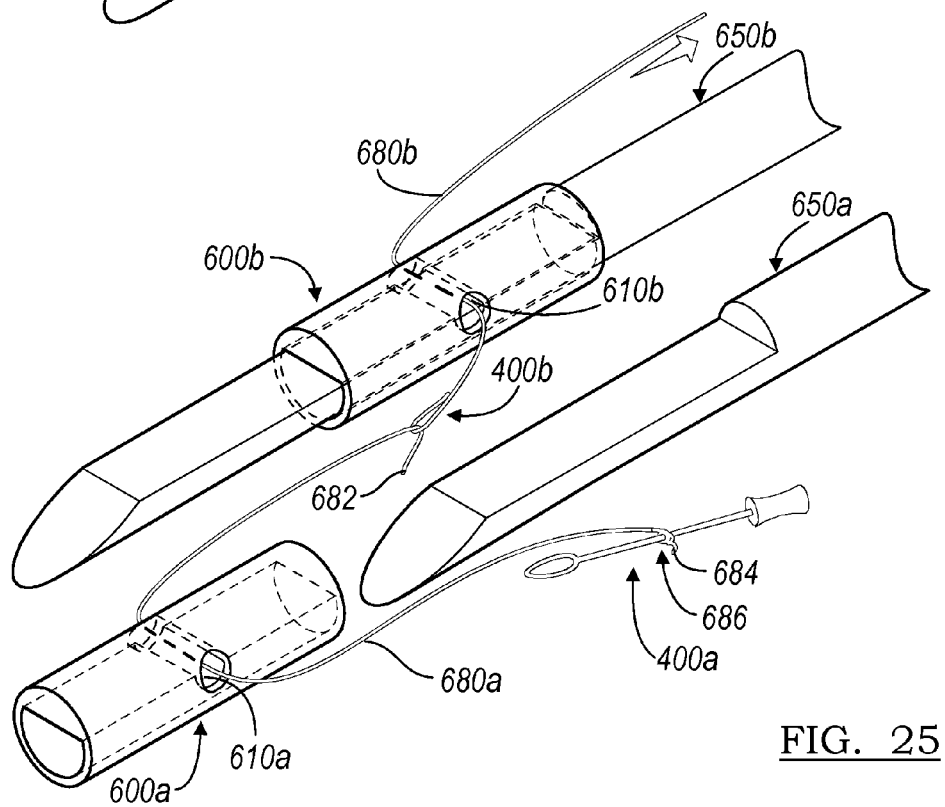
FIG. 25 is a perspective view illustrating connecting a flexible strand between first and second anchors according to the present teachings.
Figure 26:
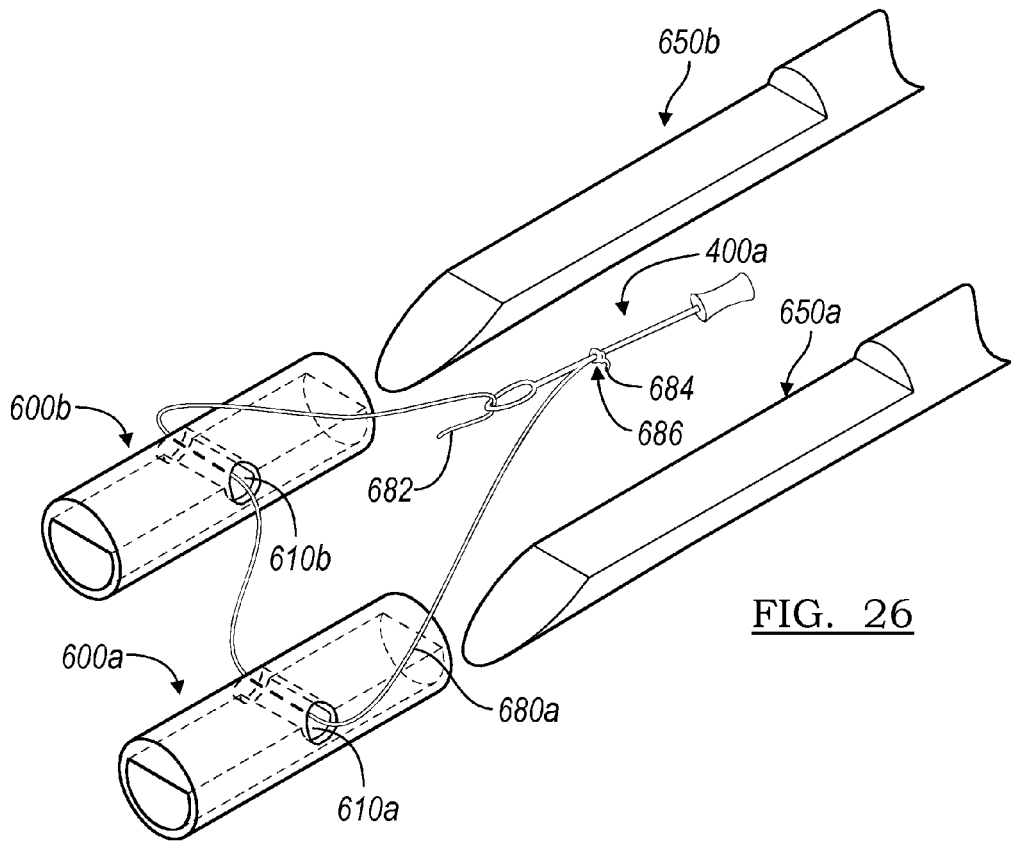
FIG. 26 is a perspective view illustrating passing a free end of flexible strand connecting first and second anchors through a slip knot according to the present teachings.
Figure 28A:
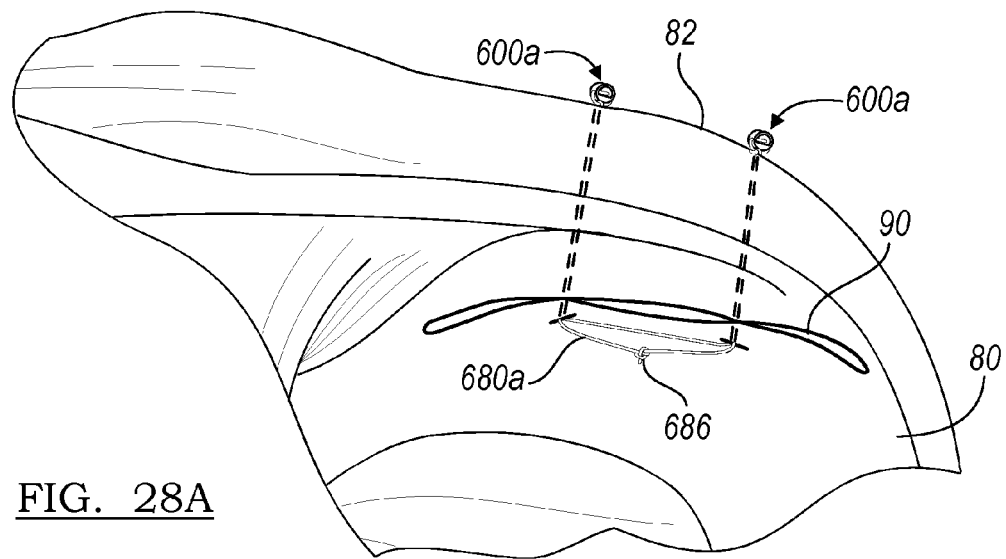
FIGS. 28A and 28B are environmental views illustrating a soft tissue defect repair with two anchors according to the present teachings.
Figure 28B:
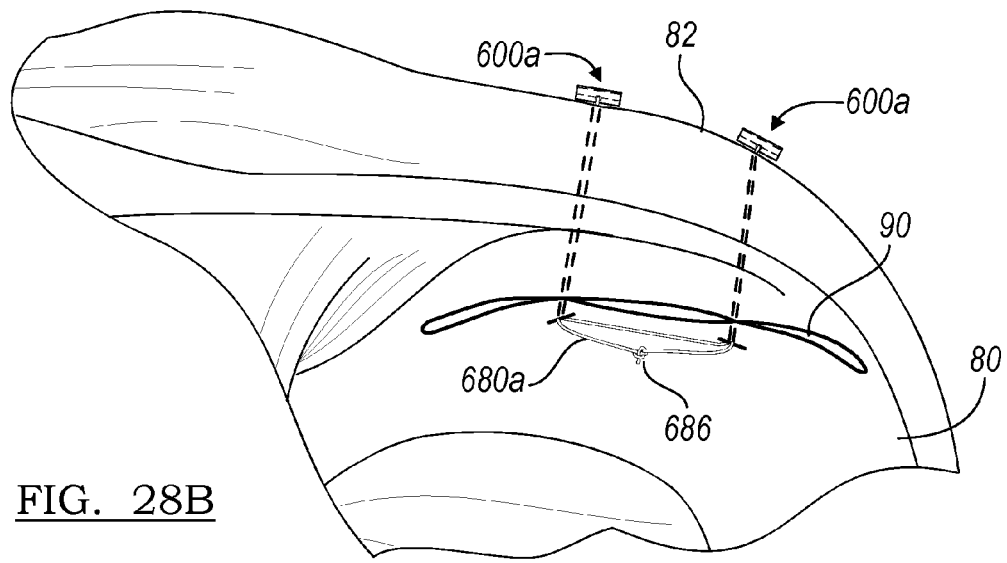

Referring to FIGS. 24-26, an alternative intra-operative strand connection for the first and second anchors 600a, 600b is illustrated in which strand loops such as loops 670a, 670b shown in FIGS. 21-23 are not used. Rather, the first inserter 650a can be assembled with the first strand 680a passing through the transverse bore 610a of the first anchor 600a and coupled to the first threader 600a, as shown in FIG. 24. Similarly, the second inserter 650b can be also assembled with the second strand 680b passing through the transverse bore 610b of the second anchor 600b and coupled to the second threader 400b. After the first anchor 600a is implanted on the second side 82 of the soft tissue 80 and the first inserter 650a is removed and discarded, the first strand 680a can be pulled by the second threader 400b through the transverse bore 610b of the second anchor 600b, as shown in FIG. 25. After the second anchor 600b is also implanted and the second inserter 650b removed and discarded, the free end 682 of the first strand 680a can be captured by the first threader 400a and passed through the slip knot 686, as shown in FIG. 26. The first strand 680 is then tensioned to reduce the defect 90, as described above and shown in FIGS. 28A and 28B.

Figure 26A:
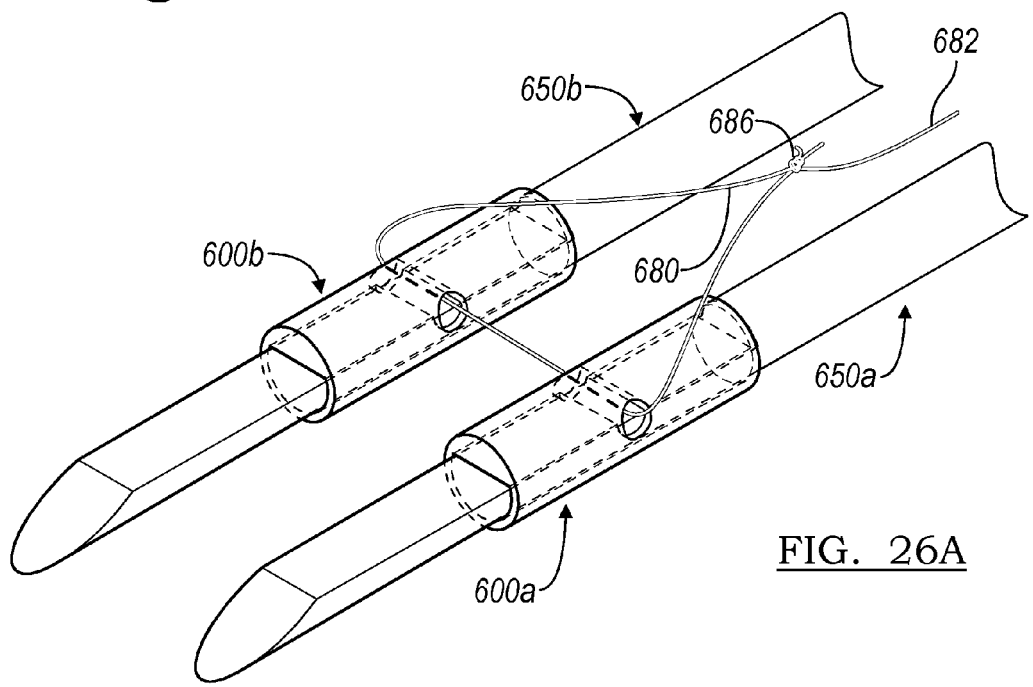
FIG. 26A is a perspective view illustrating first and second anchors connected by a flexible strand according to the present teachings.
Figure 26B:
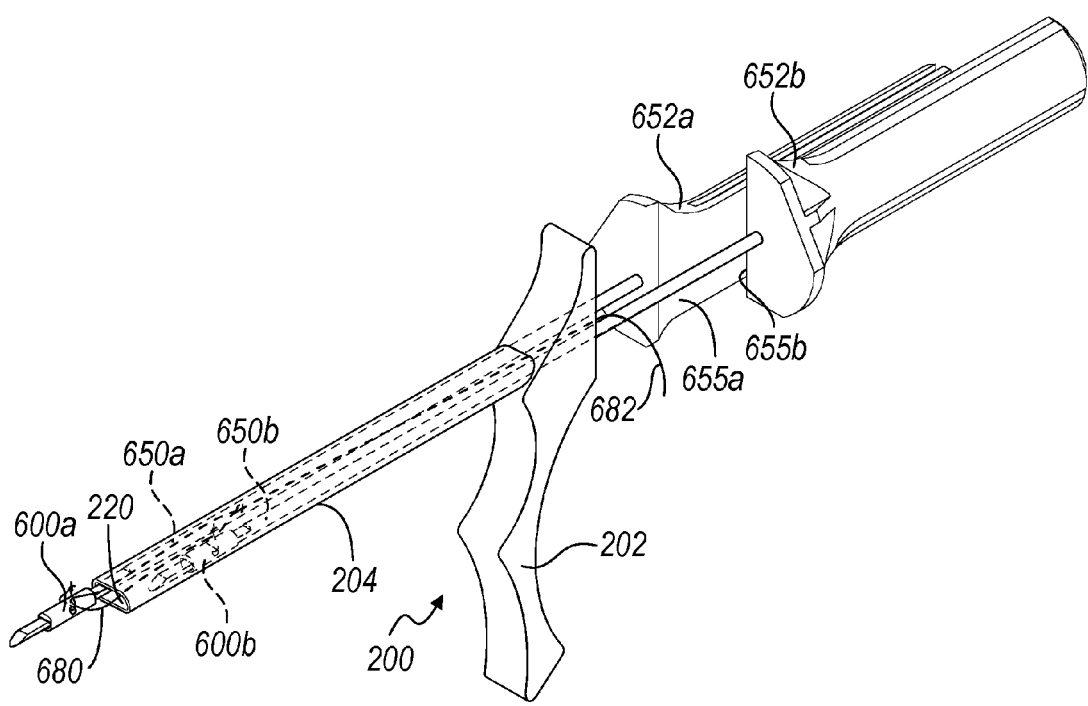
FIG. 26B is a perspective view of a soft tissue repair device according to the present teachings.

Referring to FIGS. 26A and 26B, the flexible strand 680 can be pre-loaded on the first and second anchors 600a, 600b with the free end 682 passing through the slip knot 686, as shown. The first and second anchors 600a, 600b, can be deployed as described above using the first and second inserters 650a, 650b with the interconnected anchors 600a, 600b assembled thereon. The bore 220 of the hollow shaft 204 of the cannula 200 can have an elongated shape, or an eight-like shape as described in connection with FIG. 15B above. The cannula 200 can be used for receiving both the first and second inserters 650a, 650b sequentially or simultaneously, as shown in FIG. 26B. The handles 652a, 652b of the first and second inserters 650a, 650b can have corresponding flat surfaces 655a, 655b, facing one another and slidable relative to one another, such that each of the first and second inserters 650a, 650b can be independently inserted into or retracted from the cannula bore 220 without interference or obstruction from the other.

Referring to FIGS. 29-32 and 37, various views of an inserter assembly 800 carrying first and second inserters 102a, 102b, such as those described above, are illustrated. The inserter assembly 800 can be optionally used with a cannula. The inserter assembly 800 can include a handle 802 and first and second sliders 804a, 804b operable for selectively and separately moving the corresponding inserters 102a, 102b, as described below. The handle 802 can be constructed from first and second handle portions 802a, 802b that are bonded or otherwise attached to one another.

Figure 29:
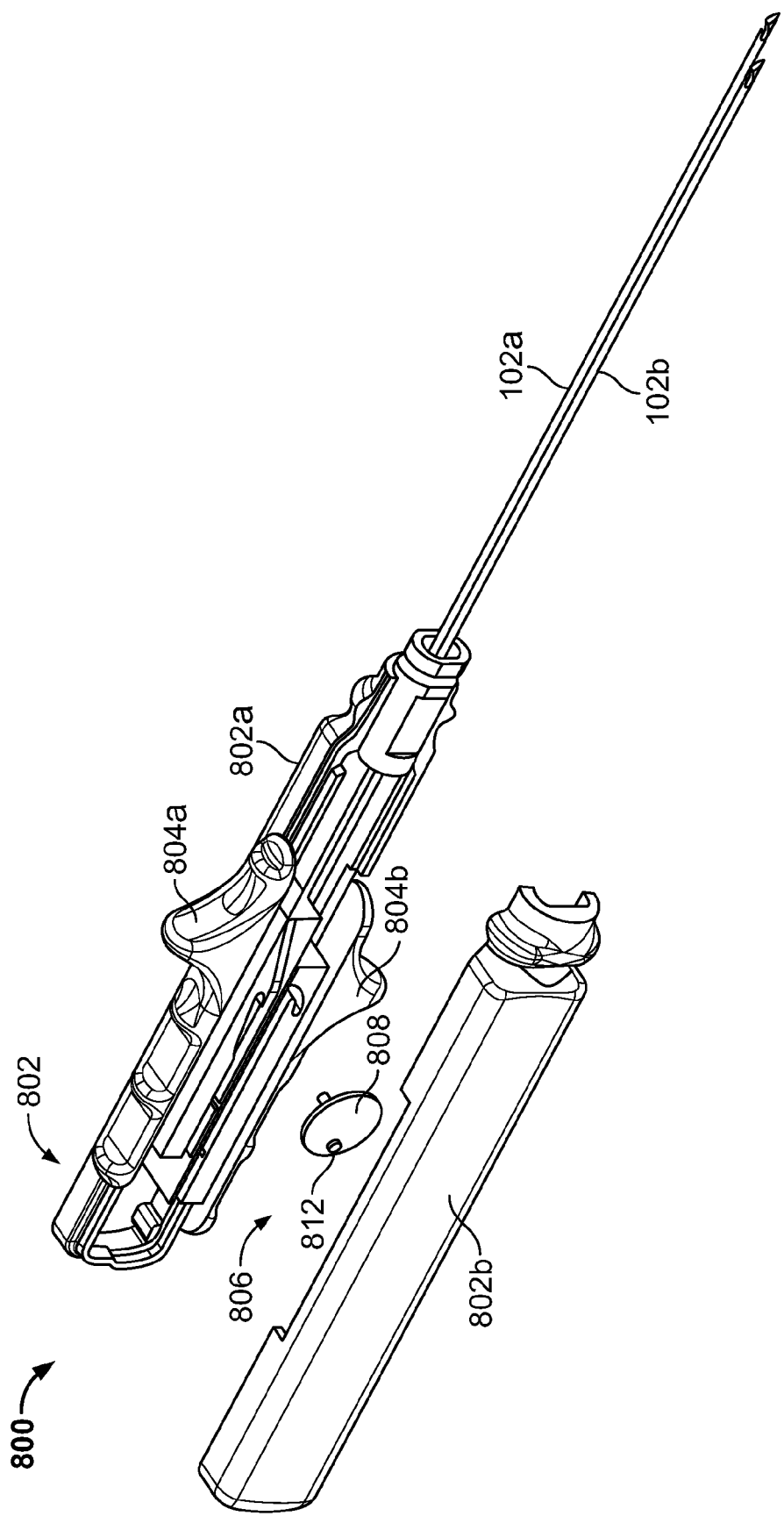
FIG. 29 is partially exploded perspective view of an inserter assembly according to the present teachings.
Figure 30:
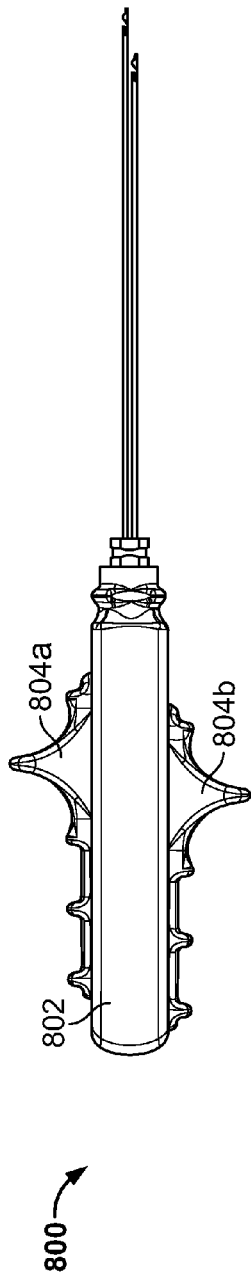
FIG. 30 is a plan view of the inserter assembly of FIG. 29.
Figure 31:
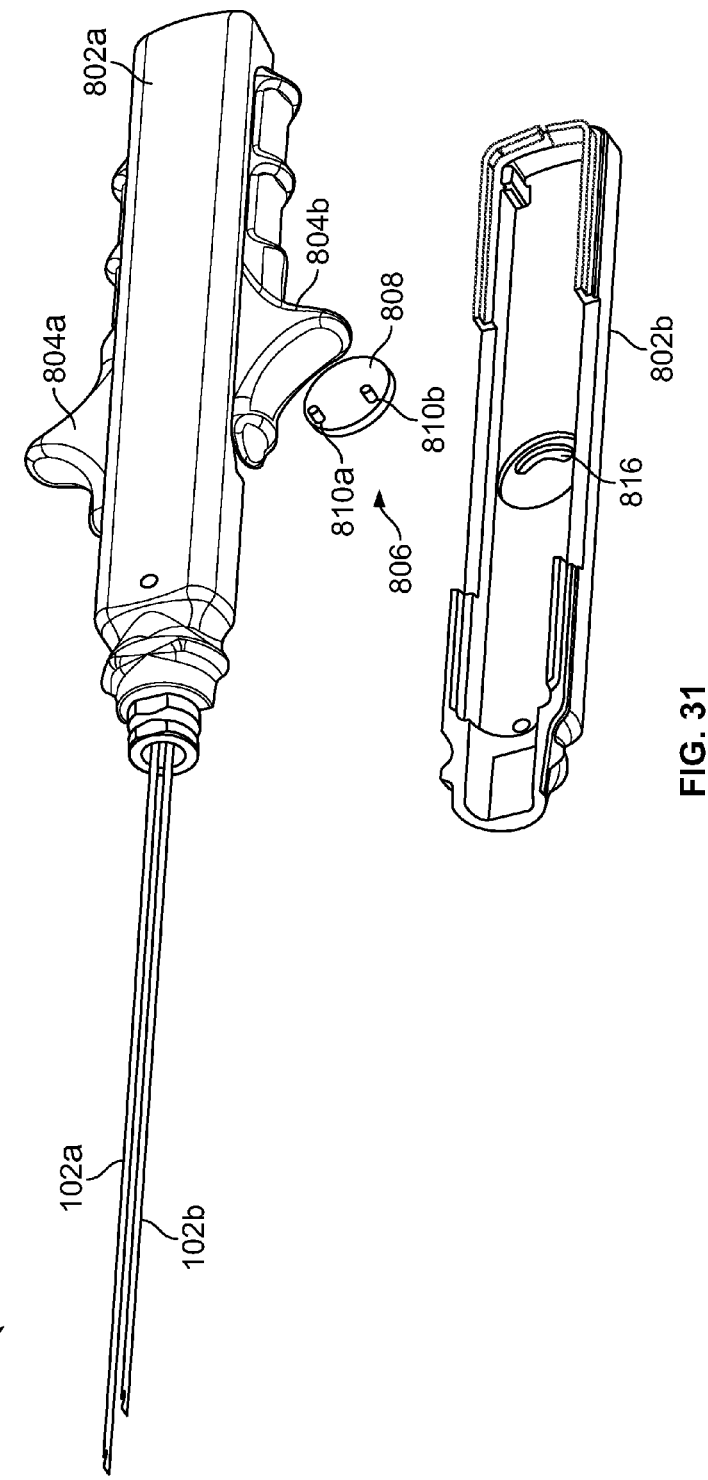
FIG. 31 is another partially exploded view of the inserter assembly of FIG. 29.
Figure 32:
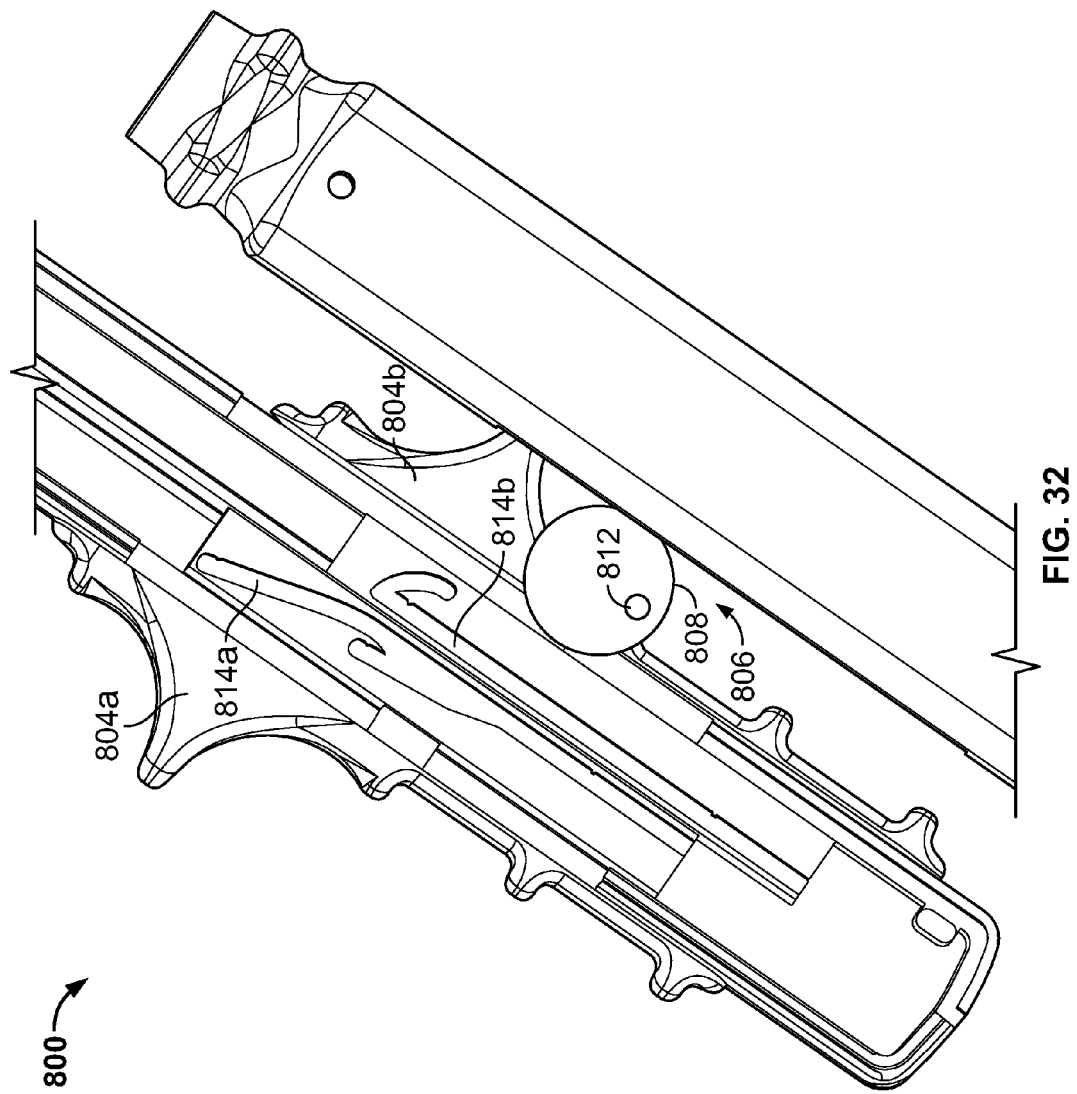
FIG. 32 is a detail of a partially exploded view of the inserter assembly of FIG. 29.
Figure 33:
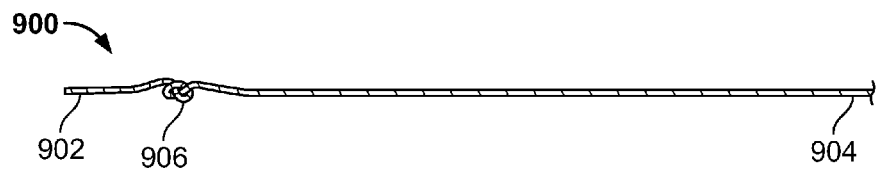
FIGS. 33, 34, 35 and 36 are sequential views illustrating an exemplary method of coupling first and second flexible anchors with a flexible strand.

In one aspect, the inserter assembly 800 can also include a slider control mechanism 806 between the first and second handle portions 802a, 802b. The slider control mechanism 806 can be coupled to the first and second sliders 804a, 805b and is operable to prioritize the separate deployment of the first and second flexible anchors 150a, 150b, which are loaded on the respective first and second inserters 102a, 102b. The slider control mechanism 806 can include a pivotable disc 808 having first and second posts or pins 810a, 810b on a first side and a third post or pin 812 on a second side opposite the first side, as shown in FIGS. 29, 31, and 32. The first and second posts 810a, 810b can move along respective first and second curved tracks 814a, 814b, respectively associated with the first and second sliders 804a, 804b. The third post 812 can move along an associated third curved track or groove 816 defined on an inner surface of the second handle portion 802b.

In one aspect, by the cooperation of the first and second tracks 804a, 804b, and the disc 808, the slider control mechanism 806 can enable a forward or deployment motion of the first inserter 102a, before enabling a retraction motion of the first inserter 102a and a subsequent forward or deployment motion of the second inserter 102b. The preferential deployment of the first inserter 102a ensures that the first anchor 150a will be deployed before the second anchor 150b, although the first and second flexible anchors 150a, 150b are substantially identical. The second anchor 150b is the anchor associated with the adjustment portion 908 and from which the free second end 904 of the flexible strand 900 exits. As discussed above, each anchor 150a, 150b can be sleeve-like having first and second ends 152, 154 and a longitudinal bore 158 extending between the first and second ends 152, 154. See also FIG. 38.

Figure 34:
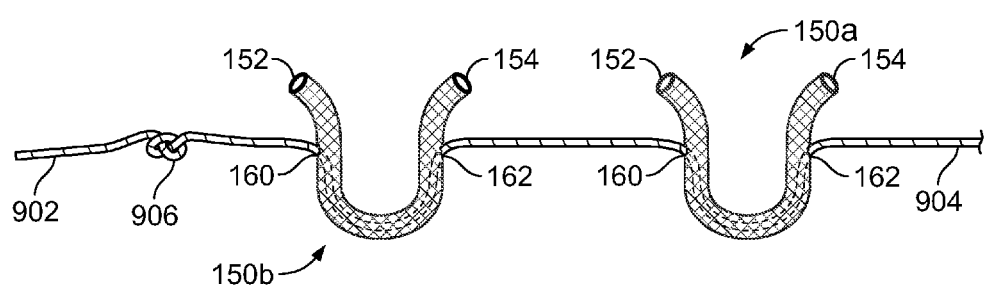

Referring to FIGS. 33-38, another aspect of coupling the flexible anchors 150a, 150b with a flexible strand 900 is illustrated. The flexible strand 900 can have first and second ends 902, 904 and can be made of materials similar to those discussed above in reference to the flexible strand 301. The flexible strand 900 can be braided in a tubular or hollow form such that it forms an internal passage 901 along the first and second ends 902, 904. A small knot or other retaining device 906 can be optionally formed adjacent the first end 902. It will be appreciated that the knot 906 can be entirely omitted. The flexible strand 900 can be passed through a first opening 160 of each flexible anchor 150a, 150b, guided along the bore 158 and exit through a second opening 162 of each flexible anchor 150a, 150b, as shown in FIG. 34. The openings 160, 162 can be positioned between the first and second ends 152, 154 of each flexible anchor 150a, 150b, at a distance of, for example one-quarter length from the ends 152, 154. Furthermore, it will be appreciated that the openings 160, 162 can be voids in the woven fabric of the flexible anchors 150a, 150b, such that the openings 160, 162 do not disrupt or break the weave of flexible anchors 150a, 150b, when the flexible anchors 150a, 150b are made of braided or woven material.

Figure 35:
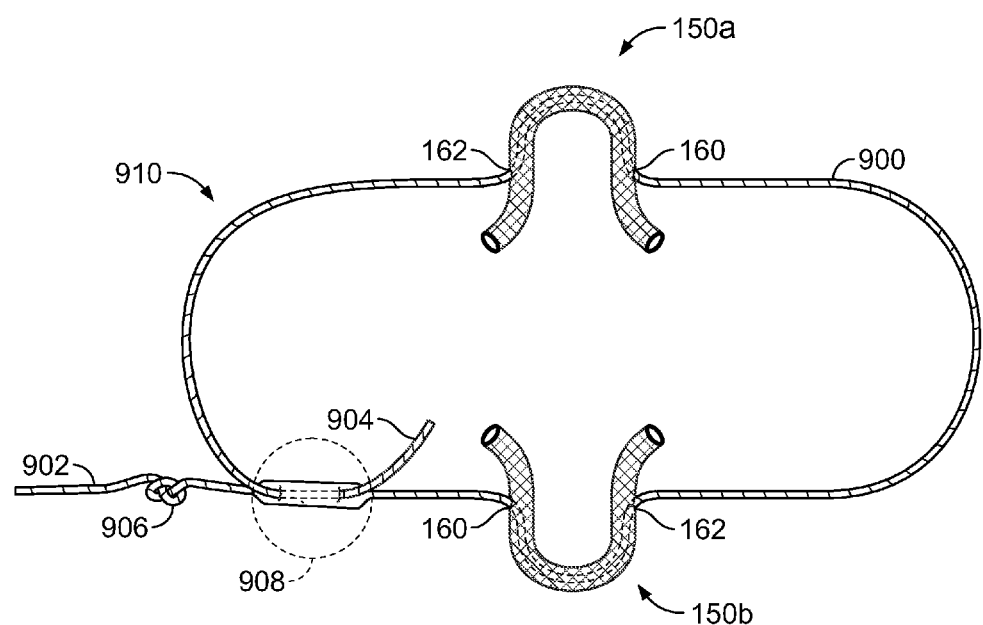
Figure 35A:
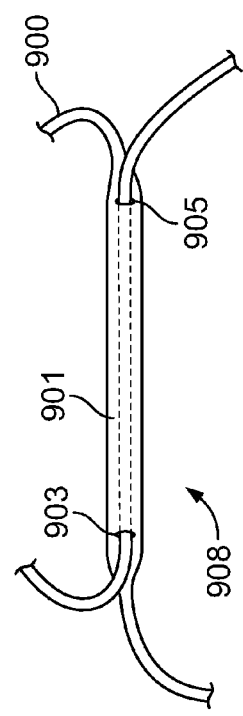
FIG. 35A shows a detail of FIG. 35.
Figure 36:
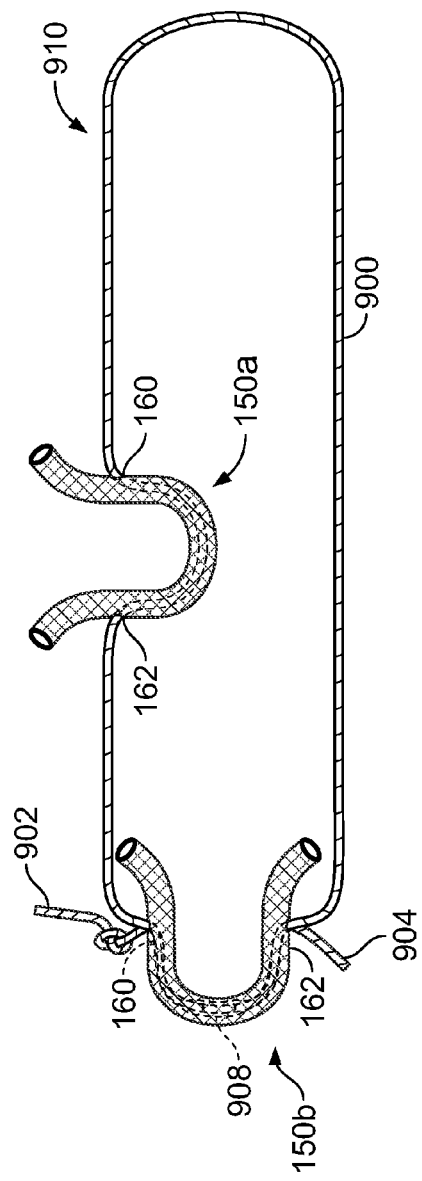

After the flexible anchors 150a, 150b are mounted on the flexible strand 900, the second end 904 of the flexible strand 900 can be passed into the internal passage 901 of the flexible strand 900 at an aperture 903, guided longitudinally along the passage 901, and guided out of the flexible strand 900 at an aperture 905. The portion of the flexible strand 900 between apertures 901 and 905 can form an adjustment portion 908 between the knot 906 and the opening 162 of the second flexible anchor 150b, such that the flexible strand 900 defines a single adjustable knotless loop 910, as shown in FIGS. 35 and 35A. The second flexible anchor 150b can be slidably moved along the flexible strand 900 until the adjustment position 908 is within the bore 158 of the second flexible anchor 150b and the knot 906 is adjacent the opening 160 second flexible anchor 150b, as shown in FIG. 36. It will be appreciated, however, that the adjustment portion 908 can remain in the position shown in FIG. 35. The adjustable knotless loop 910 is self-locking and does not require the surgeon to tie a knot during the surgical procedure for securing the flexible strand 900. Further, once the adjustable knotless loop 910 is self-locked by pulling the second end 904 of the flexible strand 900 and tensioning the flexible strand 900, friction prevents the adjustable knotless loop 910 from being loosened, thereby providing a secure lock. Additional details regarding forming the knotless adjustable loop 910 and other adjustable knotless loop configurations are disclosed in copending and commonly assigned U.S. patent application Ser. No. 11/541,506, filed on Sep. 29, 2006, the disclosure of which is incorporated herein by reference.

Figure 37:
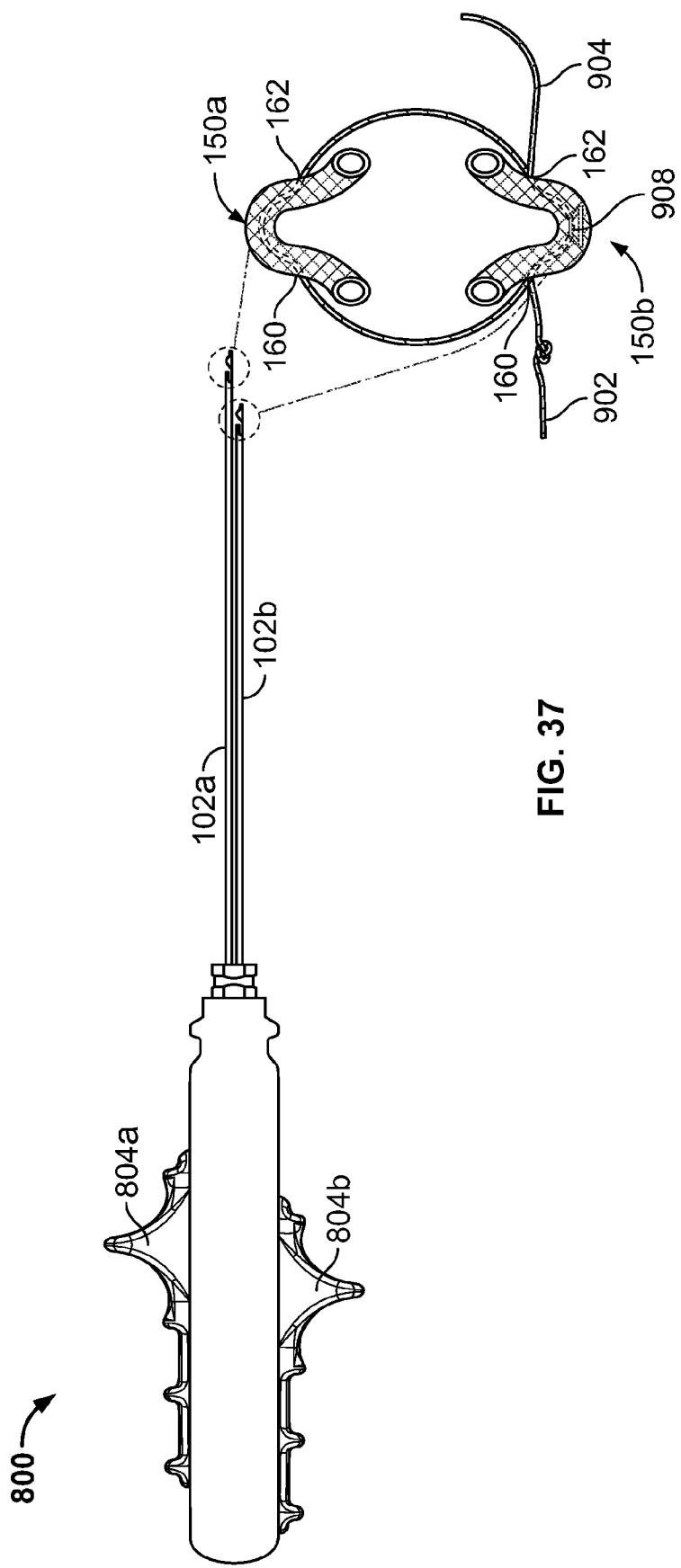
FIG. 37 is a view illustrating loading first and second flexible anchors on the inserter assembly of FIG. 29.
Figure 39A:
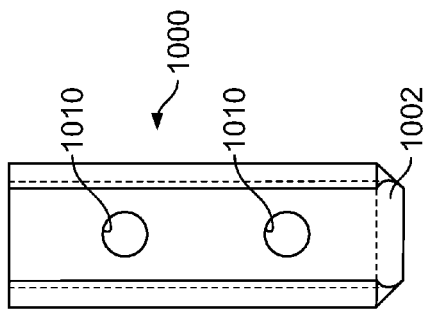
FIG. 39A is a bottom view of an anchor according to the present teachings.
Figure 39B:
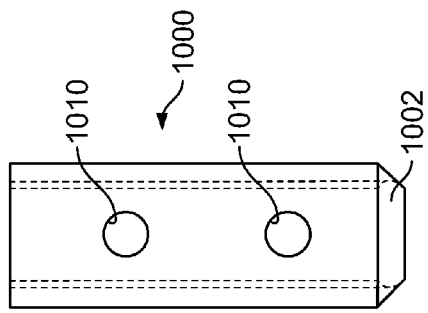
FIG. 39B is a top view of the anchor of FIG. 39A.
Figure 38:
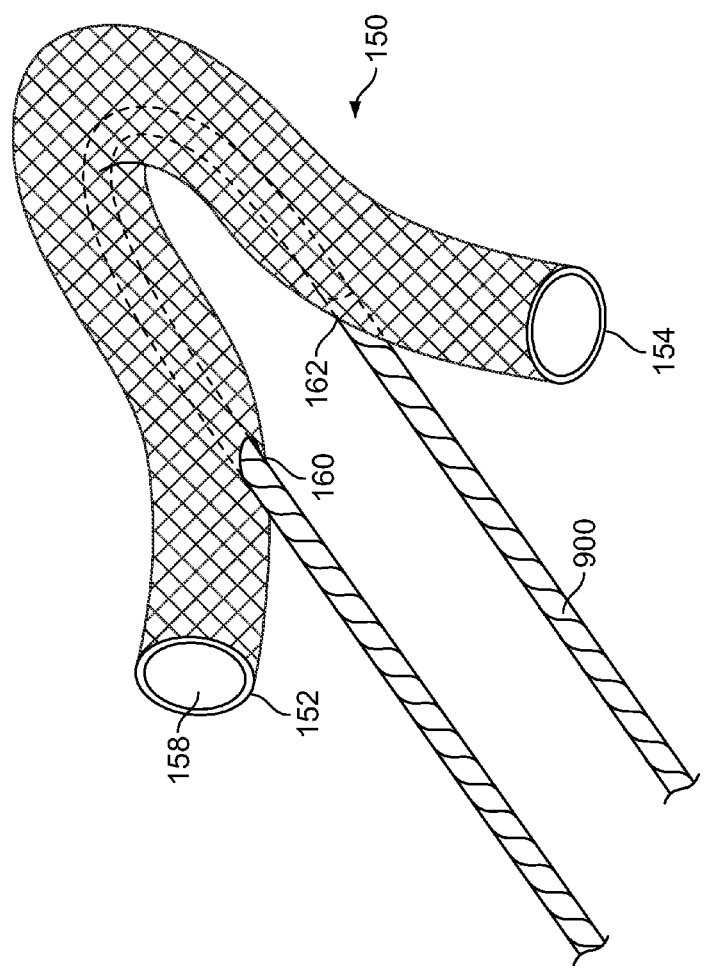
FIG. 38 is a perspective view of a flexible anchor coupled with a flexible strand.

The first flexible anchor 150a can be loaded on the first inserter 102a, and second flexible anchor 150b can be loaded on the second inserter 102b, as shown in FIG. 37. The first and second anchors 150a, 150b can be loaded externally on their respective inserters in the manner discussed in reference with FIG. 13, above. Specifically, each of the first and second flexible anchors 150a, 150b can be draped over the external groove 120 in the distal portion of the corresponding inserter 102a, 102b. The inserter assembly 800 can be loaded with the first and second flexible anchors 150a, 150b coupled with the flexible strand 900, which forms the closed adjustable knotless loop 910. The adjustable knotless loop 910 allows tightening the strand 900, deforming the first and second flexible anchors 150a, 150b for anchoring and shortening the length of the adjustable knotless loop 910 without using a slipknot. The inserter assembly 800 can be used for repairing soft tissue 80, such as a meniscus tear 90, in a similar manner as discussed with reference to FIG. 14. The first slider 804a can be moved forward to deploy the first flexible anchor 150a at an outer surface 82 of the soft tissue. The first slider 804a can then be moved backward, enabling the second slider 804b to be moved forward to deploy the second flexible anchor 150b at the outer surface 82 of the soft tissue, and adjacent the first flexible anchor 150a. Pulling the second end 904 of the flexible strand 900 tightens the adjustable knotless loop 910, secures the first and second flexible anchors 150a, 150b against the outer surface 82 of the soft tissue 80 and reduces the defect 90. Further, the portions of the sleeve between the first and second ends 152, 154 of each of the flexible anchors 150a, 150b and the corresponding first and second openings 160, 162, define anchoring leg portions that provide additional resistance for securing the flexible anchors 150a, 150b on the outer surface 82 of the soft tissue 80, as these leg portions are forced against the outer surface 82 for anchoring.

Figure 40:
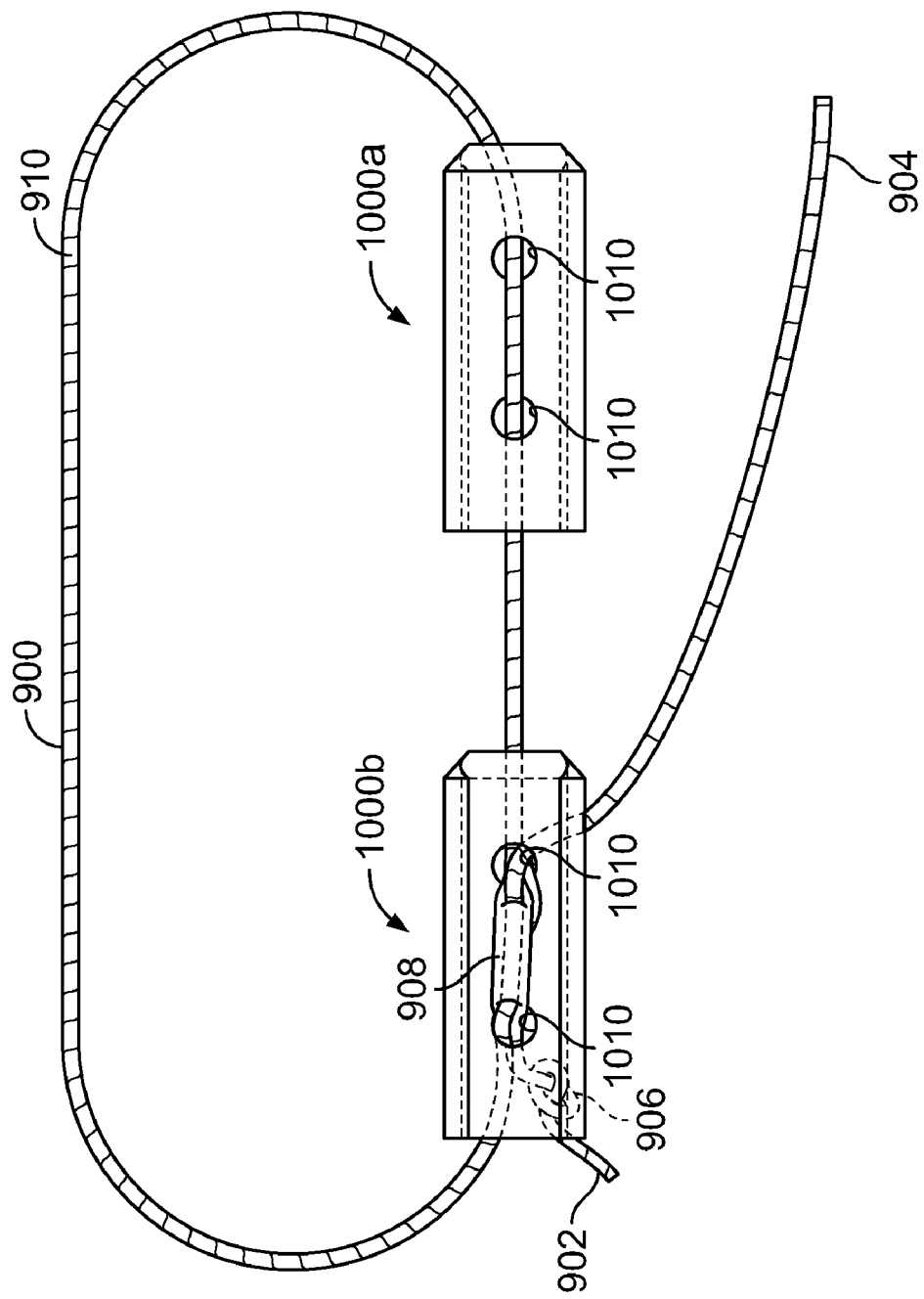
FIG. 40 is a view illustrating coupling first and second anchors with a flexible strand according to the present teachings.

Referring to FIGS. 39A-41, another non-deformable or substantially rigid anchor 1000 is illustrated. Similarly to the anchor 600 illustrated in FIG. 20, the anchor 1000 can be made of any biocompatible material, such as, for example, titanium or other non-resorbable or resorbable material, including polymeric materials and Lactosorb® commercially available from Biomet, Inc., Warsaw, Ind., and can be used in a similar manner to repair a soft tissue defect 90. The anchor 1000 can be tubular defining a longitudinal bore 1002 that extends between first and second ends 1004, 1006 of the anchor 600 and has an open, channel-like cross-section defining an arc of 180 degrees or more. The ends 1004, 1006 of the anchor 1000 have blunt rounded edges substantially perpendicular to the anchor 1000, such that the ends 1004, 1006 are not capable and not intended for piercing or penetrating tissue. The anchor 1000 can further define first and second transverse through bores 1010 oriented substantially perpendicularly to the anchor 1000. A flexible strand 900 can be passed through the transverse bores 1010 and couple first and second anchors 1000a, 1000b, as shown in FIG. 40. The strand 900 can be tightened with an adjustable knotless loop 910 by pulling on free end 904 and without the use of slipknot, as discussed above.

Figure 41:
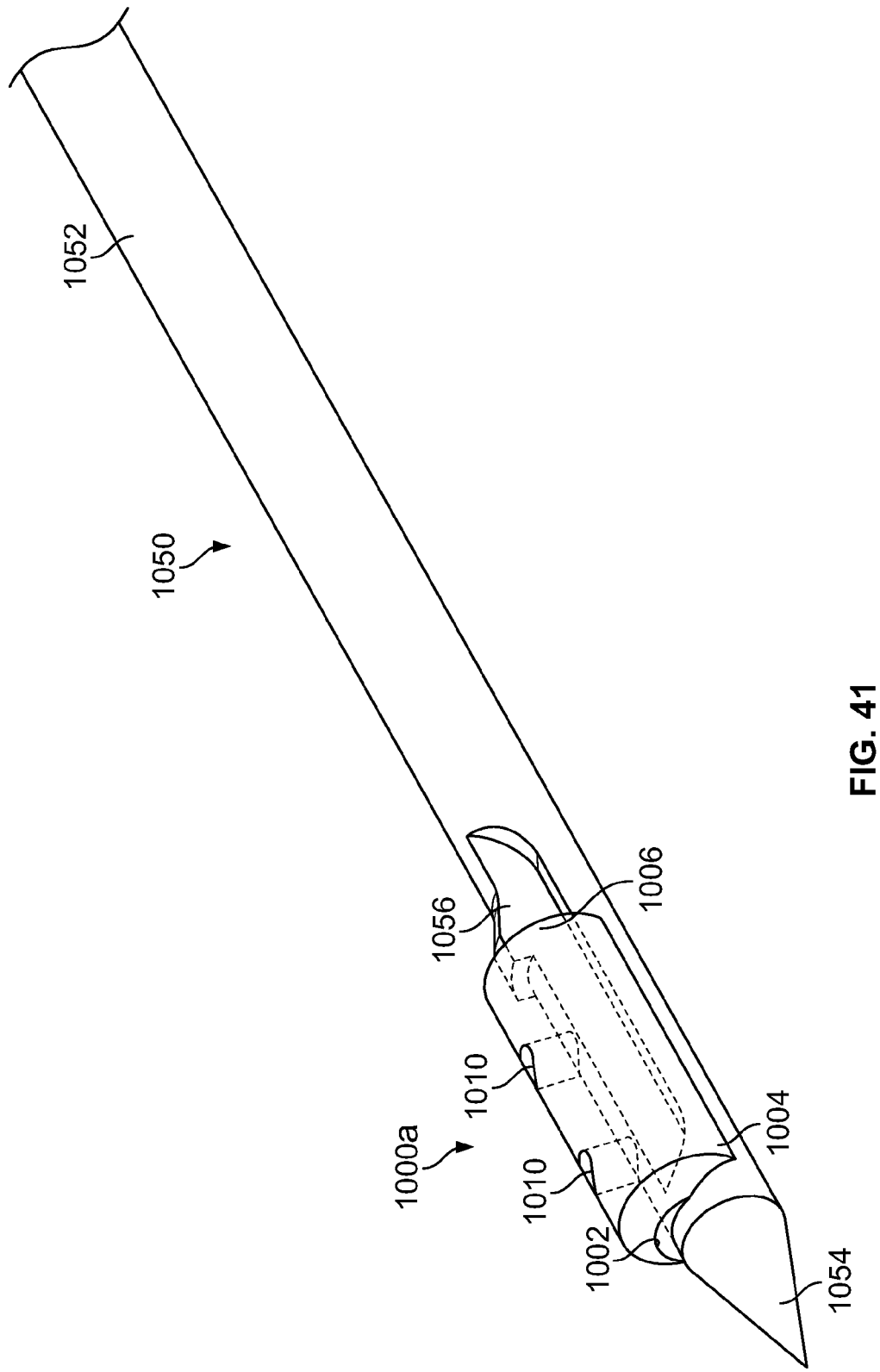
FIG. 41 is a perspective view showing an anchor loaded onto an inserter according to the present teachings.

The first and second anchors 1000a, 1000b, coupled with the flexible strand 900, can be mounted on two separate inserters, as described above in connection with anchors 600. An exemplary inserter 1050 loaded with the anchor 1000a is shown in FIG. 41. Two such inserters 1050 can be used with the inserter assembly 800 of FIG. 29, replacing the inserters 102a, 102b. Each inserter 1050 can have a cylindrical body 1052, a pointed tip 1054, and a stop 1056. The first anchor 1000a can be mounted externally onto the body 1052 of the inserter 1050 between the tip 1054 and the stop 1056, such that that a portion of the inserter 1050 is received in the longitudinal bore 1002 of the first anchor 1000a. The second anchor 1000b can be similarly mounted on another inserter 1050. Each anchor 1000a and 1000b can be optionally mounted in a keyed manner onto the corresponding inserter 1050, such that accidental relative rotation is substantially prevented.

It will be appreciated from the above description and drawings that the present teachings provide anchors of versatile configurations that can be passed through fibrous tissue easily in a compact or low profile configuration and or orientation and then positioned outside the fibrous tissue in a second orientation that provides anchoring without tissue penetration, prevents withdrawal from the tissue and reduces tissue injury. Additionally, the inserter of the present teachings does not require an active expeller or other additional pusher rod to deploy the anchor. Rather, and because the anchor is carried solely on the external surface of the inserter, the anchor is deployed passively outside fibrous tissue upon retraction of the inserter. Further, the use of a disposable or single use inserter provided with a preassembled anchor can help reduce the time length of the procedure and simplify manipulations required during the procedure.

It will be further understood that the various embodiments of the inserters, anchors and coupling arrangements can be mixed and matched or combined in ways other than those explicitly discussed above, without departing from the scope of the present teachings.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A fibrous tissue repair device comprising:
 a first tubular anchor defining a longitudinal passage between first and second ends;
 a first inserter having a longitudinal shaft along a longitudinal axis with a buttress transverse to the longitudinal axis for abutting on the first tubular anchor and a distal portion extending from the buttress and having an elongated planar surface transverse to the buttress and keyed to a planar surface of the longitudinal passage of the first tubular anchor, the distal portion received in the longitudinal passage of the first tubular anchor;
 a second tubular anchor defining a longitudinal passage between first and second ends;
 a second inserter having a longitudinal shaft having distal portion received in the longitudinal passage of the second tubular anchor; and
 a flexible strand coupling the first and second tubular anchors.

2. The repair device of claim 1, wherein the longitudinal passage of each of the first and second tubular anchors is D-shaped.

3. The repair device of claim 1, wherein the flexible strand passes through corresponding first and second bores of the first and second tubular anchors.

4. The repair device of claim 3, wherein each of the first and second bores is at an angle relative to the longitudinal passages of the corresponding first and second tubular anchors.

5. The repair device of claim 1, wherein each of the first and second tubular anchors has a circular cross-section.

6. The repair device of claim 1, wherein each of the first and second inserters passes through a cannula having a handle.

7. The repair device of claim 6, wherein each of the first and second inserters includes corresponding first and second handles coupled to the corresponding longitudinal shafts.

8. The repair device of claim 7, wherein the first and second handles include corresponding first and second flat surfaces.

9. The repair device of claim 6, wherein the cannula has an elongated cross-section.

10. A fibrous tissue repair device comprising:
- a first non-deformable anchor having a first longitudinal passage;
- a first inserter having a first longitudinal shaft with a distal portion received in the first longitudinal passage of the first non-deformable anchor and a proximal portion coupled to a first handle;
- a second non-deformable anchor having a second longitudinal passage;
- a second inserter having a second longitudinal shaft having distal portion received in the second longitudinal passage of the second non-deformable anchor and a proximal portion coupled to a second handle;
- a flexible strand coupling the first and non-deformable second anchors; and
- a cannula having a third handle and a longitudinal passage with an elongated cross-section slidably receiving the first and second longitudinal shafts;
- wherein the first and second handles have corresponding first and second elongated flat surfaces facing one another and forming a symmetric cylindrical handle when in contact, the first and second flat surfaces are configured for sliding relatively to one another.

11. The repair device of claim 10, wherein the cannula has an elongated cross-section.

12. The repair device of claim 10, wherein the flexible strand forms an adjustable loop.

13. The repair device of claim 10, wherein each of the first and second inserters includes a stop for the corresponding of first and second non-deformable anchors.

14. The repair device of claim 10, wherein the first and second non-deformable anchors have circular cross-sections.

15. The repair device of claim 14, wherein each of the first and second non-deformable anchors include corresponding first and second transverse bores.

16. The repair device of claim 15, wherein the flexible strand passes through first and second transverse bores of the corresponding first and second non-deformable anchors.

17. The repair device of claim 10, wherein the first and second longitudinal passages have D-shaped cross-sections.

18. A fibrous tissue repair device comprising:
- a first tubular anchor having a longitudinal axis and defining a longitudinal passage between first and second ends, the longitudinal passage having a D-shaped cross-section;
- a first inserter having a longitudinal shaft with a buttress for the first tubular anchor and a D-shaped distal portion having a longitudinal planar surface transverse to the buttress and extending distal from the buttress, the distal portion received and keyed in the longitudinal passage of the first tubular anchor;
- a flexible strand passing through a transverse bore of the first tubular anchor, the transverse bore perpendicular the longitudinal axis of the first tubular anchor; a second tubular anchor defining a longitudinal passage between first and second ends, the longitudinal passage having a D-shaped cross-section; a second inserter having a longitudinal shaft with a distal portion received in the longitudinal passage of the second tubular anchor, the second inserter having a buttress for the second tubular anchor; and wherein the flexible stand passes through a transverse bore of the second tubular anchor.

* * * * *

UNITED STATES PATENT AND TRADEMARK OFFICE
CERTIFICATE OF CORRECTION

PATENT NO. : 8,337,525 B2  
APPLICATION NO. : 13/045689  
DATED : December 25, 2012  
INVENTOR(S) : Kevin T. Stone It is certified that error appears in the above-identified patent and that said Letters Patent is hereby corrected as shown below:

In the Specification

Column 3, line 16, After "is" insert --a--.

Column 3, line 50, After "is" insert --a--.

Column 5, line 20, "can be also be" should be --can also be--.

Column 8, line 14, "FIG. 17-19" should be --FIGS. 17-19--.

Column 8, line 65, "anchor 60a, 600b" should be --anchor 600a, 600b--.

Column 9, line 57, "804a, 805b" should be --804a, 804b--.

Column 10, line 55, After "opening 160" insert --of--.

Column 12, line 4, Delete second occurrence of "that".

Column 13, lines 26-27, "first and non-deformable second anchors" should be --first and second non-deformable anchors--.

Signed and Sealed this  
Second Day of December, 2014

Michelle K. Lee  
*Deputy Director of the United States Patent and Trademark Office*